(12) United States Patent
Lee et al.

(10) Patent No.: US 8,368,402 B2
(45) Date of Patent: Feb. 5, 2013

(54) NMR SYSTEMS FOR IN VIVO DETECTION OF ANALYTES

(75) Inventors: W. David Lee, West Newton, MA (US); David A. Berry, Brookline, MA (US)

(73) Assignee: T2 Biosystems, Inc., Lexington, MA (US)

(*) Notice: Subject to any disclaimer, the term of this patent is extended or adjusted under 35 U.S.C. 154(b) by 631 days.

(21) Appl. No.: 12/514,250

(22) PCT Filed: Nov. 8, 2007

(86) PCT No.: PCT/US2007/023516
§ 371 (c)(1),
(2), (4) Date: Nov. 18, 2009

(87) PCT Pub. No.: WO2008/057578
PCT Pub. Date: May 15, 2008

(65) Prior Publication Data
US 2010/0072994 A1   Mar. 25, 2010

Related U.S. Application Data

(60) Provisional application No. 60/857,742, filed on Nov. 8, 2006.

(51) Int. Cl.
*G01V 3/00* (2006.01)
(52) U.S. Cl. .................. 324/321; 324/318
(58) Field of Classification Search .......... 324/321, 324/318, 309, 307, 306
See application file for complete search history.

(56) References Cited

U.S. PATENT DOCUMENTS

| | | |
|---|---|---|
| 4,101,435 A | 7/1978 | Hasegawa et al. |
| 4,452,773 A | 6/1984 | Molday |
| 4,875,486 A | 10/1989 | Rapoport et al. |
| 4,920,061 A | 4/1990 | Poynton et al. |
| 5,049,819 A | 9/1991 | Dechene et al. |
| 5,072,732 A * | 12/1991 | Rapoport et al. ............ 600/415 |
| 5,136,095 A | 8/1992 | Tarnowski et al. |
| 5,164,297 A | 11/1992 | Josephson et al. |
| 5,204,457 A | 4/1993 | Maruno et al. |
| 5,254,460 A | 10/1993 | Josephson et al. |
| 5,262,176 A | 11/1993 | Palmacci et al. |
| 5,424,419 A | 6/1995 | Hasegawa et al. |
| 5,445,970 A | 8/1995 | Rohr |
| 5,445,971 A | 8/1995 | Rohr |
| 5,492,814 A | 2/1996 | Weissleder |

(Continued)

FOREIGN PATENT DOCUMENTS

| | | |
|---|---|---|
| WO | WO 90/06045 | 6/1990 |
| WO | WO 91/17428 | 11/1991 |

(Continued)

OTHER PUBLICATIONS

Atanasijevic et al., "Calcium-Sensitive MRI Contrast Agents Based on Superparamagnetic Iron Oxide Nanoparticles and Calmodulin," *PNAS* 130:14707-14712, 2006.

(Continued)

*Primary Examiner* — Louis Arana
(74) *Attorney, Agent, or Firm* — Clark & Elbing LLP

(57) ABSTRACT

This invention relates generally to NMR systems for in vivo detection of analytes. More particularly, in certain embodiments, the invention relates to systems in which superparamagnetic nanoparticles are exposed to a magnetic field and radio frequency (RF) excitation at or near the Larmor frequency, such that the aggregation and/or disaggregation of the nanoparticles caused by the presence and/or concentration of a given analyte in a biological fluid is detected in vivo from a monitored RF echo response.

18 Claims, 11 Drawing Sheets

U.S. PATENT DOCUMENTS

| | | | |
|---|---|---|---|
| 5,572,132 | A | 11/1996 | Pulyer et al. |
| 5,801,003 | A | 9/1998 | Shimamura et al. |
| 6,013,188 | A | 1/2000 | Terstappen et al. |
| 6,165,378 | A | 12/2000 | Maruno et al. |
| 6,194,900 | B1 * | 2/2001 | Freeman et al. ............ 324/321 |
| 6,294,342 | B1 | 9/2001 | Rohr et al. |
| 6,297,062 | B1 | 10/2001 | Gombinski |
| 6,342,396 | B1 | 1/2002 | Perrin et al. |
| 6,361,944 | B1 | 3/2002 | Mirkin et al. |
| 6,489,767 | B1 | 12/2002 | Prado et al. |
| 6,500,343 | B2 | 12/2002 | Siddiqi |
| 6,599,498 | B1 | 7/2003 | Groman et al. |
| 6,600,945 | B2 | 7/2003 | Ginggen et al. |
| 6,630,355 | B1 | 10/2003 | Pivarnik et al. |
| 6,767,635 | B1 | 7/2004 | Bahr et al. |
| 6,822,452 | B2 | 11/2004 | Ham et al. |
| 6,866,838 | B1 | 3/2005 | Mondain-Monval et al. |
| 6,940,378 | B2 | 9/2005 | Miller et al. |
| 6,958,609 | B2 | 10/2005 | Raftery et al. |
| 7,001,589 | B2 | 2/2006 | Mondain-Monval et al. |
| 7,018,849 | B2 | 3/2006 | Piasio et al. |
| 7,200,430 | B2 | 4/2007 | Thomas et al. |
| 7,217,457 | B2 | 5/2007 | Elaissari et al. |
| 7,217,542 | B2 | 5/2007 | Tyvoll et al. |
| 7,332,353 | B2 | 2/2008 | Baudry et al. |
| 7,459,145 | B2 | 12/2008 | Bao et al. |
| 7,553,542 | B2 | 6/2009 | Ou et al. |
| 7,564,245 | B2 * | 7/2009 | Lee ............................. 324/321 |
| 7,781,228 | B2 * | 8/2010 | Menon et al. ............... 436/526 |
| 7,800,371 | B2 * | 9/2010 | Park et al. .................... 324/321 |
| 7,829,350 | B2 | 11/2010 | Josephson et al. |
| 8,102,176 | B2 * | 1/2012 | Lee ............................. 324/309 |
| 8,310,231 | B2 | 11/2012 | Lee |
| 8,310,232 | B2 | 11/2012 | Lee |
| 2003/0216638 | A1 | 11/2003 | Dharmakumar et al. |
| 2003/0222648 | A1 | 12/2003 | Fan |
| 2004/0018611 | A1 | 1/2004 | Ward et al. |
| 2008/0204022 | A1 | 8/2008 | Sillerud et al. |
| 2008/0305048 | A1 | 12/2008 | Josephson et al. |
| 2009/0099342 | A1 | 4/2009 | Braconnot et al. |
| 2010/0120174 | A1 | 5/2010 | Josephson et al. |
| 2011/0018538 | A1 | 1/2011 | Lee |
| 2011/0020787 | A1 | 1/2011 | Lee |
| 2011/0020953 | A1 | 1/2011 | Lee |
| 2011/0046004 | A1 | 2/2011 | Josephson et al. |
| 2011/0053174 | A1 | 3/2011 | Josephson et al. |
| 2011/0070657 | A1 | 3/2011 | Josephson et al. |
| 2012/0107839 | A1 | 5/2012 | Lee |

FOREIGN PATENT DOCUMENTS

| | | |
|---|---|---|
| WO | WO 98/04740 | 2/1998 |
| WO | WO 98/21587 | 5/1998 |
| WO | WO 01/00876 | 1/2001 |
| WO | WO 01/11360 | 2/2001 |
| WO | WO 01/19405 | 3/2001 |
| WO | WO 02/074164 | 9/2002 |
| WO | WO 02/098364 | 12/2002 |
| WO | WO 2005/061724 | 7/2005 |
| WO | WO 2005/099419 | 10/2005 |
| WO | WO 2006/122083 | 11/2006 |
| WO | WO 2007/106765 | 9/2007 |
| WO | WO 2009/026251 | 2/2009 |

OTHER PUBLICATIONS

Costanzo et al., "Protein-Ligand Mediated Aggregation of Nanoparticles: A Study of Synthesis and Assembly Mechanism," *Chem. Mater.* 16:1775-1785, 2004.

Daniel et al., "Multi-Reservoir Device for Detecting a Soluble Cancer Biomarker," *Lab Chip* 7:1288-1293, 2007.

Demas et al., "Portable, Low-Cost NMR with Laser-Lathe Lithography Produced Microcoils", *J. Mag. Resonance* 189:121-129, 2007.

Elgort et al., "A Review of Technical Advances in Interventional Magnetic Resonance Imaging," *Academic Radiology* 12(9):1089-1099, 2005.

Fry et al., "A New Approach to Template Purification for Sequencing Applications using Paramagnetic Particles," *BioTechniques* 13(1):124-131, 1992.

Gijs, "Manetic Bead Handling On-Chip: New Opportunities for Analytical Applications," *Microfluid Nanofluid* 1 :22-40, 2004.

Grimm, "Novel nanosensors for rapid analysis of telomerase activity," *Cancer Research* 64:639-643, 2004.

Josephson et al., "High-efficiency intracellular magnetic labeling with novel superparamagnetic-TAT peptide conjugates," *Bioconjugate Chem.* 10(2):186-191, 1999.

Josephson et al., "Magnetic nanosensors for the detection of oligonucleotide sequences," *Angew Chem* 40(17):3204-3206, 2001.

Kim et al., "Magnetic relaxation switch detection of human chorionic gonadotropin," *Bioconjugate Chemistry* 18(6):2024-2028, 2007.

Koschinsky et al., "Sensors for glucose monitoring: Technical and clinical aspects," *Diabetes/Metabolism Research and Reviews.* 17(2):113-123, 2001.

Kotitz et al., "Determination of the binding reaction between avidin and biotin by relaxation measurements of magnetic nanoparticles," *Journal of Magnetism and Magnetic Materials* 194:62-68, 1999.

Kriz et al., "Magnetic permeability measurements in bioanalysis and biosensors," *Anal. Chem.* 68:1966-1970, 1996.

Kriz et al., "Advancements toward magneto immunoassays," *Biosensors and Bioelectronics* 13:817-823, 1998.

Lee et al., "Microelectromagnets for the control of magnetic nanoparticles," *Appl Phys Letters* 79:3308-3310, 2001.

Lewin et al., "TAT peptide-derivatized magnetic nanoparticles allow in vivo tracking and recovery of progenitor cells," *Nature Biotechnology* 18:410-414, 2000.

Ling et al., "Magnetic relaxation-based platform for multiplexed assays," *Analyst* 135:2360-2364, 2010.

Magin et al., "Miniature magnetic resonance machines," *IEEE Spectrum* 34(10):51-61, 1997.

Makiranta et al., "Modeling and simulation of magnetic nanoparticle sensor," Proceedings of the 2005 IEEE, Shanghai, China, Sep. 1-4, 2005, pp. 1256-1259, 2005.

Malba et al., "Laser-lathe lithography- a novel method for manufacturing nuclear magnetic resonance microcoils," *Biomedical Microdevices* 5(1):21-27, 2003.

Massin et al., "Planar micricoil-based microfluidic NMR probes," *J. Magnetic Resonance* 164:242-255, 2003.

Massin et al., "Planar microcoil-based magnetic resonance imaging of cells," *Transducers, Solid-state Sensors, Actuators and Microsystems 12th Int'l conference* 2(9):967-970, 2003.

Niemeyer et al., "Self-assembly of DNA-strepavidiv nanostructrues and their use as reagents in Immuno-PCR," *Nucleic Acid Research* 27(23):4553-4561, 1999.

Peck et al., "RF microcoils patterned using microlithographic techniques for use as microsensors in NMR," Engineering in Medicine and Biology Society, Proceedings of the 15th annual international conference of the IEEE, Oct. 28-31, 1993; pp. 174-175, 1993.

Perez et al., "DNA-based magnetic nanoparticle assembly acts as a magnetic relaxation nanoswitch allowing screening of DNA-cleaving agents," *J. Am. Chem. Soc.* 124(12):2856-2857, 2002.

Perez et al., "Magnetic relaxation switches capable of sensing molecular interactions," *Nature Biotechnology* 20:816-820, 2002.

Perez et al., "Viral-induced self-assembly of magnetic nanoparticles allows the detection of viral particles in biological media," *J. Am. Chem. Soc.* 125:10192-10193, 2003.

Perez et al., "Use of magnetic nanoparticles as nanosensors to probe for molecular interactions," *Chem Bio Chem* 5:261-264, 2004.

Routley et al., "The HALO system—a light weight portable imaging system," *Magentic Resonance Imaging* 22(8):1145-1151, 2004.

Shapiro et al., "Dynamic imaging with MRI contrast agents: quantitative considerations," *Magnetic Resonance Imaging* 24:449-462, 2006.

Sillerud et al., "1H NMR detection of superparamagnetic nanoparticles at 1 T using a microcoil and novel tuning circuit," *J. Mag. Resonance* 181:181-190, 2006.

Sun et al., "Continuous analyte sensing with magnetic nanoswitches," *Small* 2(10):1144-1147, 2006.

Sun et al., "Experimental study on T2 relaxation time or protons in water suspensions of iron-oxide nanoparticles: waiting time dependence," *J Mag. Mag. Mat.* 321:2971-2975, 2009.

Syms et al., "MEMS Helmholtz coils for magnetic resonance imaging," *J. Micromech. Microeng.* 15:S1-S9, 2005.

Tong et al., "Coating optimization of superparamagnetic iron oxide nanoparticles for high T2 relaxivity," *Nano Letters* 10(11):4607-4613, 2010.

Tsourkas et al., "Magnetic relaxation switch immunosensors detect enantiomeric impurities," *Angew Chem.* 43:2395-2399, 2004.

Weissleder et al., "Cell-specific targeting of nanoparticles by multivalent attachment of small molecules," *Nature Biotechnology* 23(11):1418-1423, 2005.

Wu et al., "1H-NMR spectroscopy on the nanoliter scale for static and on-line measurements," *Anal. Chem.* 66:3849-3857, 1994.

International Search Report for PCT/US2007/023516, dated Apr. 24, 2008.

U.S. Appl. No. 13/531,899, Lee.

\* cited by examiner

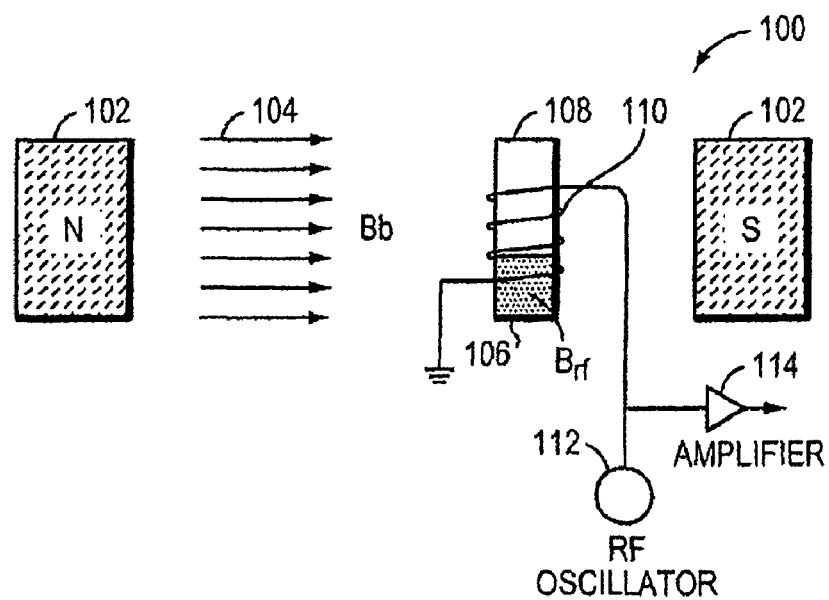
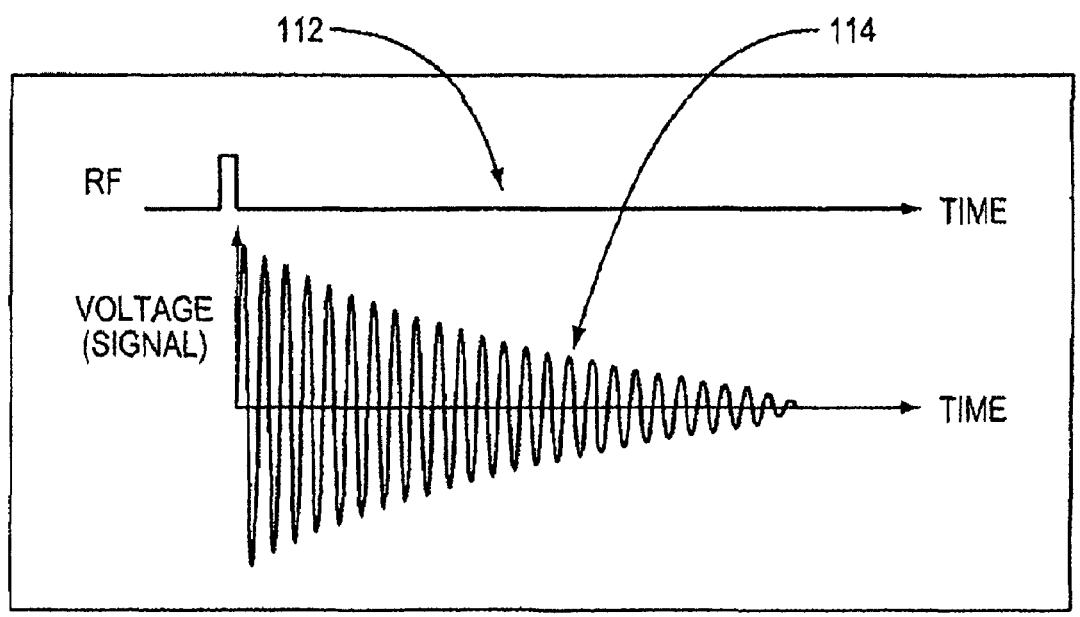
FIG. 1

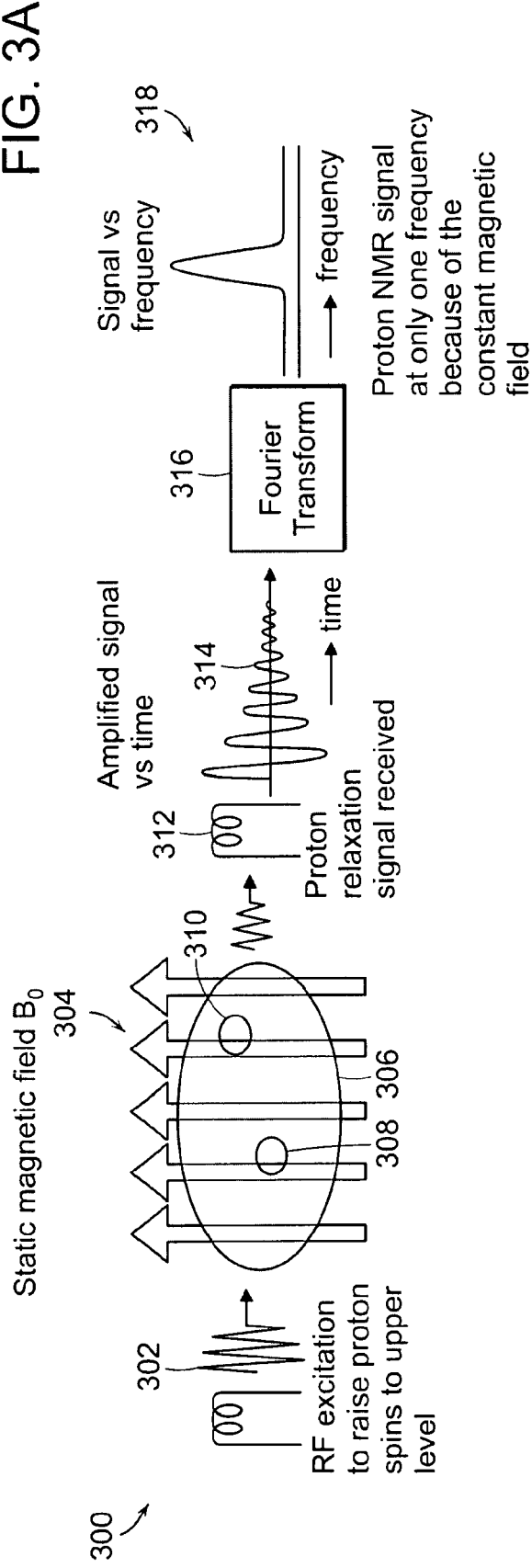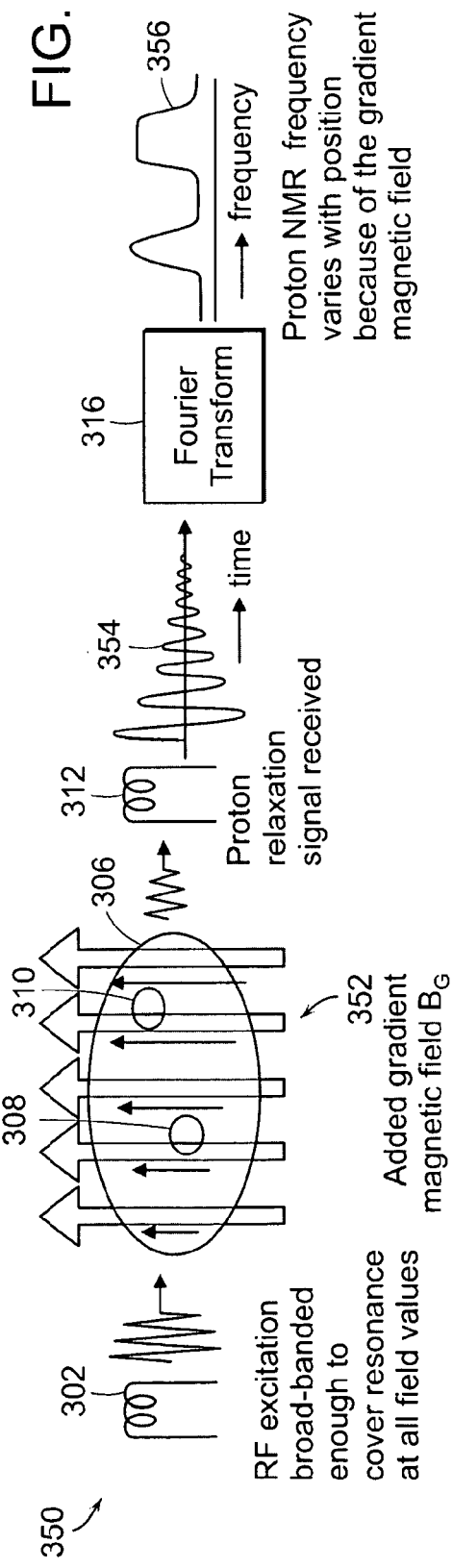

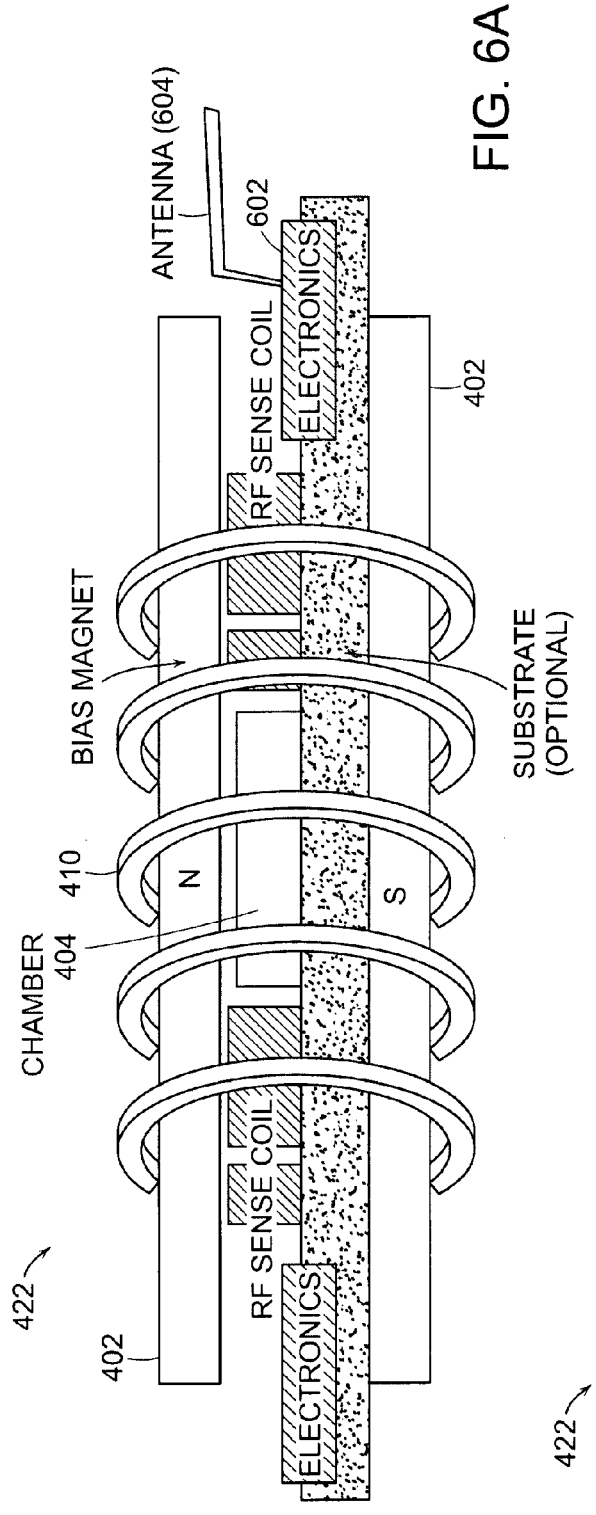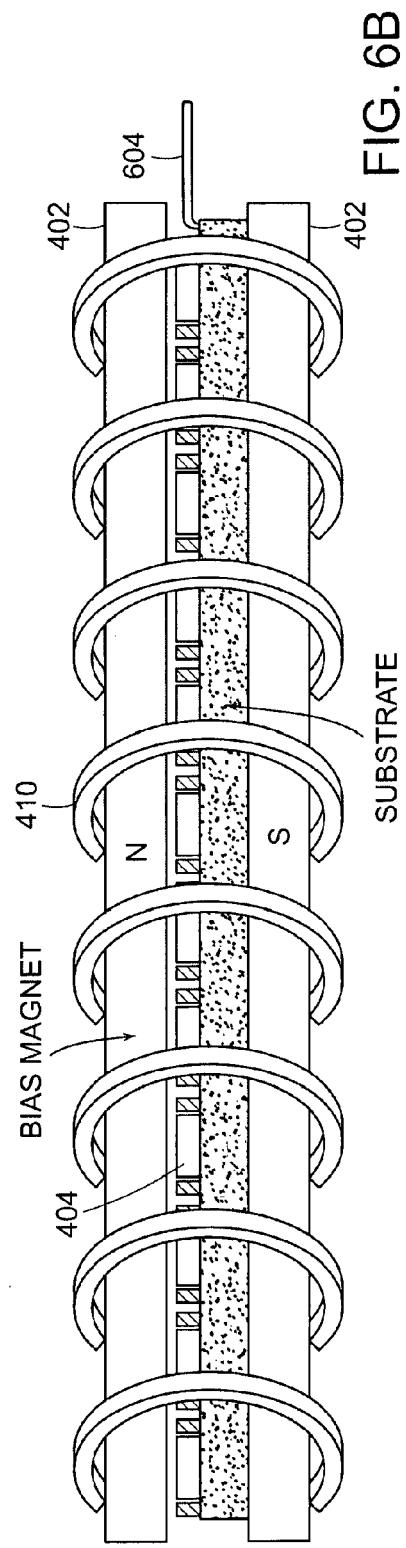

US 8,368,402 B2

NMR SYSTEMS FOR IN VIVO DETECTION OF ANALYTES

RELATED APPLICATIONS

This application is the National Stage of International Application No. PCT/US2007/023516, filed Nov. 8, 2007, which claims the benefit of U.S. Provisional Application No. 60/857,742, filed Nov. 8, 2006. The entire teachings of the above application are incorporated herein by reference.

BACKGROUND OF THE INVENTION

Biocompatible magnetic nanosensors have been designed to detect molecular interactions in biological media. Upon target binding, these nanosensors cause changes in the spin-spin relaxation times of neighboring solvent molecules of a sample, which can be detected by magnetic resonance (NMR) techniques. Thus, by using these nanosensors in a liquid sample, it is possible to detect the presence of an analyte at very low concentration—for example, small molecules, specific DNA, RNA, proteins, carbohydrates, organisms, and pathogens (e.g. viruses)—with sensitivity in the low femto-mole range (from about 0.5 to about 30 fmol).

In general, magnetic nanosensors are derivatized superparamagnetic nanoparticles that form clusters (aggregates) or nanoassemblies as a function of the presence or concentration of their intended molecular target. It is thought that when superparamagnetic nanoparticles assemble into clusters and the effective cross sectional area becomes larger, the nanoassembly becomes more efficient at dephasing the spins of surrounding water (or other solvent) protons, leading to the measurable change of the relaxation rates (1/T2).

Additionally, nanoassembly formation can be designed to be reversible (e.g., by temperature shift, chemical cleavage, pH shift, etc.) so that "forward" or "reverse" assays can be developed for detection of specific analytes. Forward (clustering) and reverse (declustering) types of assays can be used to detect a wide variety of biologically relevant materials. Furthermore, the spin-lattice relaxation time (T1) is considered independent of nanoparticle assembly formation and can be used to measure concentration in both nano-assembled and dispersed states within the same solution.

Examples of magnetic nanosensors are described in Perez et al., "Use of Magnetic Nanoparticles as Nanosensors to Probe for Molecular Interactions," *Chem Bio Chem*, 2004, 5, 261-264, and in U.S. Patent Application Publication No. US2003/0092029 (Josephson et al.), the texts of which are incorporated by reference herein, in their entirety.

Current diagnostic systems involve, for example, microarray technology, polymerase chain reaction (PCR), in situ hybridization, antibody-based immunoassays (e.g. enzyme-linked immunosorbant assays), chemiluminescence, nephelometry, and/or photometry. Generally, these systems cannot perform the diversity of assays at high sensitivity that is possible with an NMR-based nanosensor system.

Various non-NMR-based point of care bio-assays have been developed, such as portable blood glucose meters that operate using test strips impregnated with glucose oxidase. However, these systems generally lack the sensitivity, calibration, and maintenance that a laboratory setting provides. These portable systems also lack the sensitivity that is possible with NMR-based nanosensor systems, and they cannot be easily adapted for multiple analyte detection.

The above-cited Josephson et al. and Perez et al. documents describe applications of NMR relaxation methods with nanosensors using off-the-shelf relaxometers and MRI units. However, these units require large RF coils and magnets and are bulky and expensive.

There is a need for NMR-based analyte detection systems capable of in vivo use.

SUMMARY OF THE INVENTION

One embodiment of the present invention is a nuclear magnetic resonance system for assessing the presence or concentration of an analyte contained in a body fluid of a mammal in-vivo, the system comprising: (a) a sensor suitable for partial or complete implantation within the mammal's body, the sensor comprising structure defining a sample volume and a port to allow the analyte to enter the sample volume, the sample volume containing magnetic particles, the extent of aggregation of the magnetic particles being indicative of the presence or concentration of the analyte in the sample volume, (b) a reader for disposition outside the mammal's body, the reader providing results based on sensor indication of presence or concentration of the analyte in the sample volume, (c) a magnet or magnetic field generator; (d) a radiofrequency coil for applying a radiofrequency pulse sequence to the sample volume in the presence of a magnetic field provided by the magnet or magnetic field generator; and (e) means for determining the position of the sensor within the mammal's body.

Another embodiment of the present invention is a method for assessing the presence or concentration of an analyte contained in a body fluid of a mammal in-vivo using a nuclear magnetic resonance system, the method comprising the steps of: (a) implanting partially or completely a sensor of the nuclear magnetic resonance system within the mammal's body, the sensor comprising structure defining a sample volume and a port to allow the analyte to enter the sample volume, the sample volume containing magnetic particles, the extent of aggregation of the magnetic particles being indicative of the presence or concentration of the analyte in the sample volume; (b) positioning a reader of the nuclear magnetic resonance system outside the mammal's body; (c) determining the position of the sensor within the mammal's body; (d) calculating Larmor frequency within the sample volume or a portion thereof based on the position of the sensor determined in step (c); (e) applying a probe radiofrequency pulse sequence at or near the Larmor frequency to part or all of the sample volume in the presence of a magnetic field to induce echo radiofrequency signals; and (f) assessing the presence or concentration of the analyte from the echo radiofrequency signals.

Another embodiment of the present invention is a nuclear magnetic resonance device for assessing the presence or concentration of an analyte contained in a body fluid of an mammal in-vivo, the device comprising: (a) a conduit having an inlet for receiving the body fluid; (b) a sensor comprising structure defining a sample volume and a port to allow the analyte from the body fluid to enter the sample volume, the sample volume containing magnetic particles, the extent of aggregation of the magnetic particles being indicative of the presence or concentration of the analyte in the sample volume; (c) a magnet or magnetic field generator for applying a magnetic field to the sample volume; (d) a radio frequency coil for transmitting a probe radiofrequency pulse sequence at or near the Larmor frequency of water within the sample volume to the sample volume in the presence of the magnetic field to induce emission of echo radiofrequency signals from the water within the sample volume; (e) a radio frequency coil for receiving the echo radiofrequency signals; and (f) logic circuitry for calculation of a nuclear magnetic resonance parameter influenced by the presence or concentration of the analyte within the sample volume.

Another embodiment of the present invention is a surgical method comprising: (a) sampling intra-operatively a body fluid from a position within a patient's body using the aforementioned device; (b) determining a real time concentration for an analyte in the body fluid; and (c) processing the real time concentration to determine whether to remove tissue at or near the position within the patient's body from which the body fluid was sampled.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a schematic diagram of an NMR system for detection of an echo response of a sample to an RF excitation, according to an illustrative embodiment of the invention.

FIG. 3A is a schematic diagram of in vivo RF excitation of a biological sample in the presence of a uniform magnetic field, according to an illustrative embodiment of the invention.

FIG. 3B is a schematic diagram of in vivo RF excitation of a biological sample in the presence of a non-uniform magnetic field, according to an illustrative embodiment of the invention.

FIG. 6A is a schematic diagram of an implanted unit in the NMR system of FIG. 4B, according to an illustrative embodiment of the invention.

FIG. 6B is a schematic diagram of an implanted unit in the NMR system of FIG. 4B, where there are a plurality of nanoparticle-containing chambers, according to an illustrative embodiment of the invention.

DETAILED DESCRIPTION OF THE INVENTION

Figure 2:
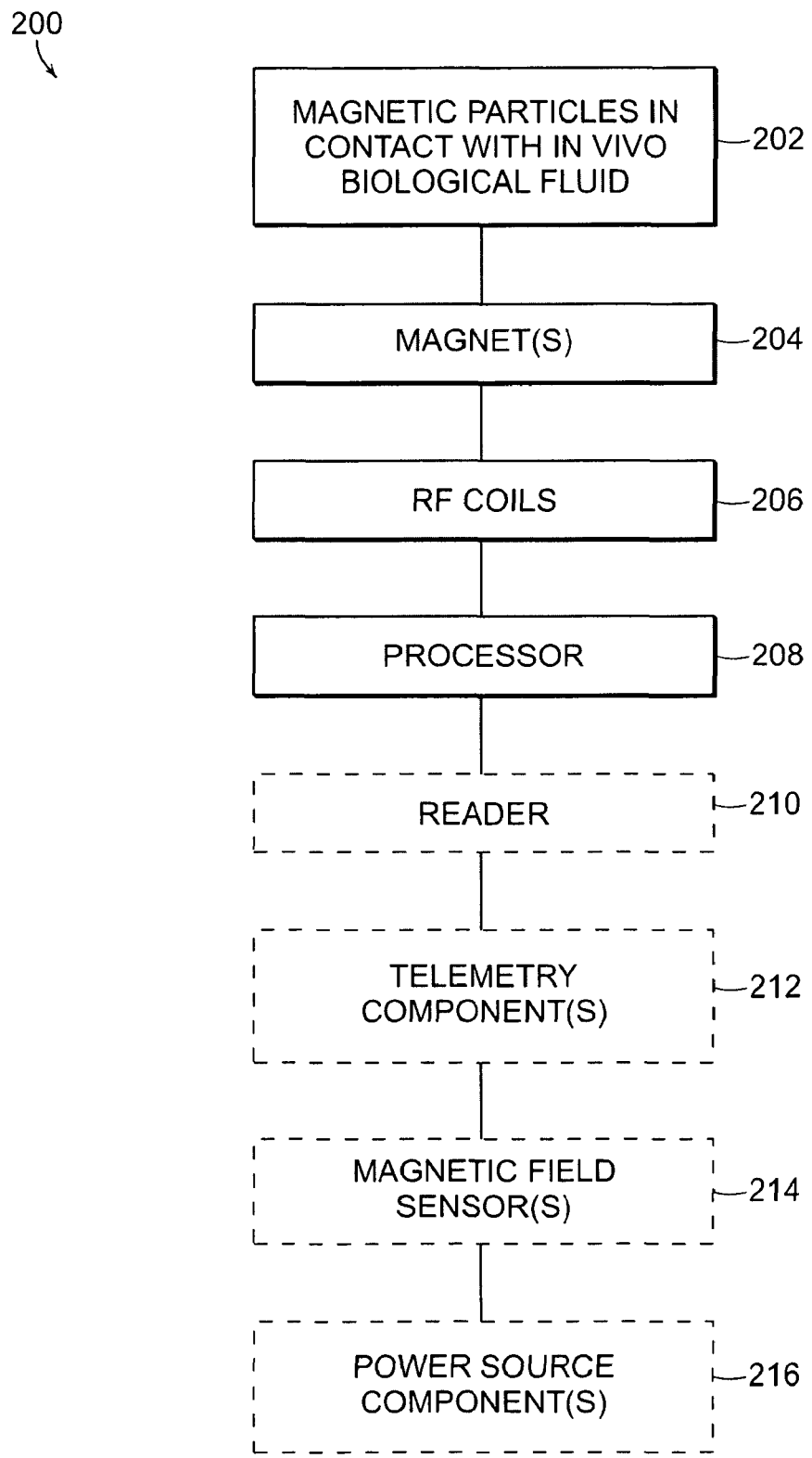
FIG. 2 is a block diagram of components of an NMR system for in-vivo detection of an echo response of a sample to an RF excitation, according to an illustrative embodiment of the invention.

The invention provides NMR-based systems for assessing the presence and/or concentration of one or more analytes in vivo in a biological fluid. The systems contact nanoparticles in vivo with a biological fluid and provide an RF excitation at the appropriate wavelength, such wavelength being a calculable function of magnetic field strength at the measured volume. The RF excitation produces one or more detectable RF echo signals representative of the degree of aggregation or disaggregation of the particles within the measured volume, which is a function of the concentration or presence of the analyte in the volume. The presence and/or concentration of the analyte within the volume can then be determined from the detected RF echo signal(s).

Use of RF excitation at a particular wavelength or within a narrow bandwidth provides improved sensitivity of the in vivo detection system. Systems of the invention make possible the use of RF excitation with a narrow bandwidth, because the analyte to be detected in each chamber is known and may be predetermined, and the functionalized nanoparticles may be customized for detection of the specific analyte. However, in certain embodiments, RF excitation may cover resonances at multiple magnetic field values within an area of interest, for example, where there are multiple chambers and/or where a received echo signal is used to provide both sensor volume location information and NMR parameter(s) such as T2.

Methods and/or systems of the invention may be used, for example, to obtain real time feedback about analyte concentration (relative and/or absolute) in a body, for example, in an emergency room, operating room, ICU, hospital, physician's office, clinic, home, and/or ambulance setting.

One class of methods and corresponding devices embodying the invention dwell within the body for hours, days, or significantly extended periods, reporting (e.g. when triggered) the presence or concentration of a preselected analyte to a reader outside the body. A preferred feature of these devices is that they can be passive, i.e., they preferably do not require batteries or power leads, but rather function continuously or intermittently as demanded by an operator of the reader.

Another class of devices involves the incorporation of a sensor in communication with a fluid stream such as the lumen of a needle or catheter, or an extracorporeal shunt such as a dialysis system, which carries or collects body fluid such as blood, serum, lymph, CSF, etc, and conducts an analysis of one or more components therein. These can be connected directly to power and data transmission lines, and therefore are less complex in their design and easier to calibrate. These devices are useful during surgery, in intensive care, in the emergency room, and/or in outpatient physicians' offices, for example. Intraoperatively, these devices may be used to determine concentration (relative and/or absolute) of one or more analyte(s) as they change during a procedure or as a function of position within the body.

Devices of the invention may be used, for example, in parathyroid adenoma surgery, where the diseased gland may be identified intraoperatively by measuring in real time using a device and method of the invention the output of its hormone or other marker, and then removed. In other settings, a catheter device may be used to monitor in vivo a biological fluid, enabling rapid assessment of the presence or concentration of analytes (e.g., drugs). For example, devices of the invention may be used to monitor potassium levels in a patient suffering from hypo- or hyper-kalemia, or to monitor glucose or glycated hemoglobin (HbAlc) levels in a patient suffering from diabetes. A needle device may be used to monitor analytes within body compartments (e.g., organs, glands, veins, arteries, lumens, and the like) in real time, such as in a physician's office.

In certain embodiments in which a tuned system is employed, a sensor is placed in a calibrated magnetic field (nonuniform or uniform). If both the magnetic field strength and the nanoparticle composition of the sensor are known (or measurable), the Larmor frequency at the sensor can be determined. T2 (and/or other related NMR parameters) can be measured routinely and accurately by initiating the correct stimulatory frequency, e.g., from a coil inside or outside the body, (e.g., an ex vivo excitation coil associated with a reader) and measuring the echo signals (from which T2 can be calculated) sensed by a coil disposed in vivo or ex vivo about the sensor volume.

Where the sensing coil is in vivo, an echo signal indicative of T2 (or deduced analyte concentration), may be transmitted outside the body to permit further processing (if needed) and display of results to a technician or physician using the system. This can be done, for example, via an antenna associated with the sensor which emits a signal to a receiver outside of the body, e.g., associated with the reader. Power for the transmission can be by on board batteries of a pulse of RF applied outside the body (RFID-like). Alternatively, this can be done using a transmission line or cable.

In yet another embodiment, incorporated with the analyte sensor (adjacent or within) in vivo is a magnetic field strength sensor (any one of a number of forms-conventional circuit elements) coupled to an electrically powered or RF stimulated reporter circuit. Upon application of a magnetic field from outside the body, the magnetic field sensor emits a signal through an antenna indicative of the strength of the magnetic field at its location at a point adjacent or within the sensor volume. This signal is detected by a receiver in the reader, and again, enables the reader to infer the field strength at precise locations within the sensor volume, to calculate the corresponding Larmor frequency, and to obtain a reproducible and precise T2 from within the sensor, and thus the data needed to determine the concentration of the analyte.

Over time there will be variability of the signal for set concentrations caused by divers biochemical factors, e.g., changes will occur in particle agglomeration behavior because of variations in fluid viscosity, possible variations in temperature, degradation of binding events, breakdown of particles, and the like. The T2 reading and real concentration accordingly should be correlated for calibration purposes at least once, and if the sensor is in-dwelling for days, weeks or longer, recalibrated periodically. Calibration may be performed by measuring the T1 signal, which can provide an absolute concentration of particle in the solution. Alternatively, calibration may be achieved by including a sample of known concentration that interfaces in a controlled manner with the measurement cell for a short time specifically for this purpose. Additionally, a separate cell with similar setup and a common amount of particle with a known analyte concentration could be used. Finally, more invasive approaches, such as using a probe could be used, or connections that enable an interface through the skin (e.g. wires) can be used.

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, the term "reader" refers to apparatus, in various configurations and comprising various components as disclosed herein, typically disposed ex vivo. The reader may have: a display or reporter circuit that indicates sensed concentration; logic circuitry that converts sensed signals into concentration values (relative and/or absolute); a memory for storing data characterizing magnetic field strength and gradient, and calibration data; optionally a biasing natural magnet or electromagnet of planar, toroidal, or another configuration; a sensing RF coil; a stimulating RF coil (or one coil serving both purposes); a power supply; and/or on-board or associated positioning determining apparatus.

As used herein, the term "sensor" or "analyte sensor" refers to one or more small chambers exposed to body fluids in vivo, and containing confined paramagnetic particles having surface derivatized with binding moieties such that the extent of agglomeration of the particles is a function of the presence or concentration of a preselected analyte. In general, said extent of agglomeration affects an RF echo signal produced by RF excitation in a magnetic field. In various embodiments, the analyte sensor may also include additional components disposed in vivo (such as biasing magnets, a magnetic field sensor, or RF excitation or sensing coils) as disclosed herein.

As used herein, the term "port" refers to a structure or device that allows one or more analytes to enter and/or exit the sample volume, and may prevent other sample components to enter the sample volume. The port can be, for example, a structural part of the sensor or a separate structure attached to or contained within the sensor. Furthermore, the port can be, for example, a structure with one or more openings, a semipermeable membrane, or the like. Preferably, the port allows analytes that lead to aggregation of the magnetic particles in the sample volume to enter the sample volume and prevents sample components that would hinder the aggregation process from entering the sample volume. A port also prevents assay components, for example, magnetic particles, from leaving the device.

Preferred mammals of the present invention are non-primates (e.g., a cow, pig, horse, sheep, rabbit, guinea pig, rat, cat, dog, and mouse), more preferred mammals are primates (e.g., a monkey, chimpanzee and a human), and most preferably the mammal is a human.

A description of example embodiments of the invention follows.

FIG. 1 is a schematic diagram 100 of an NMR system for in vivo detection of an echo response of a liquid sample to an RF excitation, thereby detecting the presence and/or concentration of an analyte in the liquid sample. A bias magnet 102 establishes a bias magnetic field Bb 104 (uniform or non-uniform) through a biological fluid sample 106 which contains magnetic nanoparticles. Detection may be "in vivo" in the sense that analysis of fluid/tissue takes place while the fluid/tissue is in the body (whether or not one or more components of the system are also within the body). The in vivo detection techniques/systems described herein may be used, for example, to obtain one-time measurements, serial measurements with repeated, random, semi-random, or intermittent periods of time between reads, rapid but discrete measurements, pseudo-continuous, semi-continuous, and/or continuous measurement/monitoring of one or more analytes. The in vivo analysis may be performed, for example, with one time penetration (e.g., with a needle), repeated penetrations (e.g., with a needle), continuous penetration (e.g. with wires and/or a catheter), internally (e.g., with implanted component(s) and continuous monitoring), and/or long term (e.g. with a catheter and continuous monitoring).

An RF coil 110 and RF oscillator 112 provides an RF excitation at, near, or including the Larmor frequency, which is a linear function of the bias magnetic field Bb (and may vary with the biological fluid sample). Where the magnetic field is non-uniform, the Larmor frequency will vary with position. If the non-uniform magnetic field is known, and the location of the sampling volume is known in relation to the magnetic field, then the Larmor frequency can be computed for the desired sampling volume. As described in more detail later, it is possible to position a plurality of sensing coils, for example, a phased array of sensing coils, to detect and/or distinguish signals (e.g. locator signals and/or echo response signals) from one or more sampling chambers in vivo. Also as described in more detail later, it is possible to apply a known gradient magnetic field and tune one or more RF excitation and/or sensing coils accordingly, in order to distinguish locator and/or echo signals from different sampling chambers.

In FIG. 1, the RF coil 110 is wrapped around an implanted sample chamber 108 containing the nanoparticles. It is possible to use one or more sensing coil(s) located in proximity to the implanted sampling chamber(s), where the sensing coil(s) may be located inside the body, outside the body, or both. The excitation RF creates instability in the spin of the water protons (or free protons in a non-aqueous solvent). In general, when the RF excitation is turned off, the protons "relax" to their original state and emit an RF signal characteristic of the concentration of the analyte. The coil 110 acts as an RF antenna and detects an "echo" of the relaxation. In certain embodiments, the echo of interest is the decay in amplitude of a train of sequential echos over time (generally 10-300 milliseconds) called the T2 signal. Where determination of "T2" is described herein, it is contemplated that "change in T2" can be determined, or other attribute(s) of T2 may be determined as well. The same holds for other NMR parameters. The RF signal from the coil 110 is amplified 114 and processed to determine the T2 (decay time) response to the excitation in the bias field Bb. Other parameters may be determined in addition or in the alternative, for example, T1, T2*, and/or T1ρ may be determined in vivo, thereby providing information about the sample.

A single pulse may be delivered, or a sequence of pulses may be delivered. Various sequences of pulses (also referred to herein as "radiofrequency pulse sequence") which may be used include, for example, spin echo sequences, inversion recovery sequences, gradient echo sequences, diffusion pulse sequences, saturation recovery sequences, echoplanar pulse sequences, spiral pulse sequences, and the Carr-Purcell-Meiboom-Gill (CPMG) modified spin echo sequence. Pulse sequences may be programmed, for example, to determine or "select" positions or slices and/or to refocus measurements following a positioning/orienting pulse or pulse sequence, thereby providing increased accuracy, precision, and/or signal-to-noise ratio. Preparation pulse sequences may also be used to allow removal of artifacts (e.g. "saturation" pulse sequences to saturate unwanted protons, such as protons outside an area of interest, prior to data acquisition). 2D and/or 3D NMR techniques may be employed for location determination, analyte detection, and/or concentration measurement.

FIG. 2 is a block diagram 200 of components of an NMR system for in-vivo detection of an echo response of a sample to an RF excitation. Element 202 of the system in FIG. 2 are magnetic particles, which are in contact with the biological fluid being examined in vivo. The biological fluid may include, for example, blood, serum, urine, lymph fluid, spinal fluid, CSF, mucus, and/or other fluids that are present in a human or animal (e.g. mammal) body. Magnetic particles 202 of the system include, for example, superparamagnetic particles, paramagnetic particles, and/or magnetic particles, with sizes, for example, of between about 1 nm and about 5 μm, between about 1 nm and about 100 nm, between about 1 nm and about 60 nm, between about 1 nm and about 50 nm, between about 1 nm and about 40 nm, between about 1 nm and about 30 nm, between about 1 nm and about 20 nm, between about 1 nm and about 10 nm, between about 1 nm and about 5 nm. Alternatively, the particles, may be of sizes less than about 100 nm in at least one dimension (e.g., diameter), less than about 60 nm, less than about 50 nm, less than about 40 nm, less than about 30 nm, less than about 20 nm, less than about 10 nm, or less than about 5 nm in at least one dimension (including or in absence of the attached binding moieties). The magnetic particles 202 include the nanoparticles described in co-pending, co-owned U.S. patent application Ser. No. 11/513,503, (the '503 application) filed Aug. 31, 2006, which is incorporated herein by reference. Also described in the incorporated/attached '503 application, which may be used in embodiments described herein, are binding moieties, oligonecleotide binding moieties, polypeptide binding moieties, and antibody binding moieties. The systems described herein may be used for detecting/monitoring one or more of the biologically active substances described in the '503 application, for example, in the diagnosis, management, and/or treatment of one or more of the medical conditions described in the '503 application.

The nanoparticles may be in the form of conjugates, that is, a magnetic nanoparticle with one or more binding moieties (e.g. an oligonucleotide, nucleic acid, polypeptide, or polysaccharide) linked thereto. The binding moiety causes a specific interaction with a target analyte (or an aggregation-inducing molecule, such as avidin). The binding moiety specifically binds to a selected target analyte, for example, a nucleic acid, polypeptide, or polysaccharide, or the binding moiety can be designed to bind to another binding moiety to form an aggregate that is cleaved by the target molecule. Binding causes aggregation of the conjugates, resulting in a decrease of the spin-spin relaxation time (T2) of adjacent water protons in an aqueous solution (or free protons in a non-aqueous solvent). Cleavage causes dispersal of the aggregate into separate conjugates, resulting in an increase of the spin-spin relaxation time (T2) of adjacent water protons in an aqueous solution (or free protons in a non-aqueous solvent). Aggregates may be, for example, from about 100 to about 200 nm in at least one dimension (e.g. diameter).

Element 204 of the system depicted in FIG. 2 represents one or more magnets to provide a magnetic field over the examined volume (e.g. a volume including one or more chamber(s) containing biological fluid and magnetic particles). The one or more magnet(s) 204 may be implanted, external to the body, or both. Examples of magnet(s) 204 that can be used are described in co-pending, co-owned U.S. patent application Ser. No. 11/513,503, filed Aug. 31, 2006, which is incorporated herein by reference. The magnet(s) may be, for example, permanent bias magnets that provide a bias magnetic field of sufficient strength over the liquid sample being examined. A bias magnetic field with strength, for example, from about 1 to about 2 Tesla (or as high as 7 Tesla or more) may be achieved where proximity of the magnet to the liquid sample is facilitated by micro design and/or the in vivo, integrated, and/or implanted nature of the system. Resistive magnets and/or superconducting magnets may be used additionally or alternatively to permanent magnets, particularly in embodiments in which the magnets are external to the body.

The magnetic field may be, for example, either uniform or non-uniform in the vicinity of the measurement location(s) of the biological fluid. The magnet(s) providing the field may be, for example, rare earth magnets, e.g. neodymium magnets such as $Nd_2Fe_{14}B$ (neodymium-iron-boron), and/or samarium cobalt magnets such as $SmCo_5$. The magnetic field provided by the magnet(s) may be, for example, less than about 7 T, less than about 5 T, less than about 4 T, less than about 3 T, less than about 2 T, at about 1 T, less than about 1 T, at about 0.5 T, or less than about 0.5 T. Also, as described in more detail herein, if a non-uniform magnetic field is established, it may be necessary to determine the strength of the magnetic field at the location of the chamber(s) being analyzed. Knowing the magnetic strength allows computation of Larmor frequency, for example.

For example, one or more magnetic field sensor(s) located at or in the vicinity of the chamber(s) may be used to quantify magnetic strength at the location(s) of interest. It may further be necessary to determine the location of the chamber(s) containing the biological fluid being analyzed in vivo in order to determine the magnetic strength at the location(s) of interest. In certain embodiments, a calibrated non-uniform magnetic field is used, such that the field gradient is known as a function of position. As described more herein, it is possible to apply a known gradient magnetic field and tune one or more RF excitation and/or sensing coils accordingly, in order to distinguish locator and/or echo signals from different sampling chambers. Where magnetic field varies in space, the corresponding Larmor frequency for a given volume varies as well. One or more gradient coils and/or gradient magnets may be used to create a magnetic field gradient, for example, a gradient superimposed on a main magnetic field for selective spatial excitation. It is possible to vary a main magnetic field so that a plurality of signals can be distinguished by associating a frequency with a corresponding location.

Element 206 of the system of FIG. 2 represents one or more radio frequency (RF) coil(s). The system includes one or more RF coils 206 that provide an excitation RF pulse (and/or sequence of pulses), and that sense an echo response from biological fluid. A given RF coil may be used for both excitation of a volume with an RF pulse/pulse sequence and sensing a resulting echo response from the volume (transmitter-receiver coil), or the RF coil may be devoted solely to excitation of a volume with an RF pulse/pulse sequence (transmitter coil) or sensing an echo response from the volume (receiver coil). The RF coil(s) operate in concert with (and/or are controlled using) a processor 208. The processor 208 may include components located inside and/or outside the body. For example, the processor 208 may include circuitry (and/or other electrical components) located on or in an implanted sensor, where the circuitry is configured to at least partially process an RF signal received from an implanted RF coil in the vicinity (e.g. surrounding) a volume of biological fluid of interest. Alternatively, or in addition, the processor may include circuitry (and/or other electrical components) located outside the body, for example, in a reader, for analyzing the received or transmitted echo signals (or signals corresponding to such echo signals). The processor 208 may determine the Larmor frequency for a known location, given a measurement of magnetic field strength at that location. Additionally, the processor 208 may determine the location by methods described in more detail herein. The determined "location" may be a depth, an x,y location, both a depth and an x,y location, or simply an association of a received echo signal (or portion thereof) with a given chamber of the implanted sensor (whether or not the exact x,y,z location of the chamber is known). In certain embodiments, location is determined in Cartesian, cylindrical, and/or spherical coordinates for example.

The coils may include, but are not limited to, the coils described in co-pending, co-owned U.S. patent application Ser. No. 11/513,503, filed Aug. 31, 2006, which is incorporated herein by reference. These include, for example, micro NMR coil designs including wound solenoid coils, planar coils, MEMS solenoid coils, MEMS Helmholz coils, and saddle coils. Any other known RF coil, of any size, may be used in various embodiments. For example, where either or both the RF excitation coil(s) and the RF sensing coil(s) are located outside the body, they may be conventional RF coils used in NMR applications, such as magnetic resonance imaging (MM). For example, multi-turn solenoid, bird cage coils, single turn solenoid, and/or saddle coils may be used, for example, as transmitter-receiver coils and/or as transmitter coils. Surface coils, planar coils, solenoid coils, volume coils, quadrature coils and/or phased array coils may be used, for example, as receiver coils.

FIGS. 3A and 3B schematically illustrate relationships between magnetic field strength, sampling chamber/sensor location, Larmor frequency, and received echo signal, such relationships being used in various embodiments of the invention by the processor 208 to determine needed variables for application of appropriate excitation pulse/pulse sequence and/or interpretation of received (sensed) echo signal(s) from the one or more chambers of the sensor. FIG. 3A is a schematic diagram 300 of in vivo RF excitation of a biological sample in the presence of a uniform magnetic field $B_0$ 304. In this example, a uniform magnetic field 304 is present throughout the volume containing the sensor 310, where the sensor contains at least two chambers for in vivo analysis of biological fluid—chambers 308 and 310. The RF excitation coil 302 may be implanted, or may be located outside the body, e.g., in a band wrapped around or otherwise applied to the body at an area of interest. Where the magnetic field is uniform, the hydrogen spin-flip frequency is the same for all parts of the sample. Once excited by the RF signal, the hydrogens return to their lower energy state (relaxation) and re-emit RF radiation at their Larmor frequency (the echo signal). FIG. 3A shows this echo signal 314 detected as a function of time. The signal may be digitized and/or otherwise processed. Taking a Fourier transform 316 results in a plot of signal intensity as a function of frequency. In general, there is a proton NMR signal at one frequency (or, within a narrow frequency band) because of the constant magnetic field. Distinguishing signals from each of a plurality of sampling chambers (308, 310) may be performed, for example, by using implanted sensing coils 312 (e.g. micro coils positioned around or in proximity to the individual chambers), in which case there is generally some signal processing performed before transmitting received signals to a reader located outside the body. The signals are associated with their respective chambers. Distinguishing signals from a plurality of sampling chambers (308, 310) may also be performed by using a phased array of sensing coils (explained in more detail herein).

In general, it is preferable to use RF excitation within a narrow bandwidth. Sensitivity of the in vivo detection system is improved by the ability to use narrow bandwidth. A wider bandwidth must be used when it is not clear what frequency is to be detected; however increased bandwidth results in increased noise. Use of a narrower bandwidth results in less noise (and increased signal-to-noise ratio, S/N), but may not be possible unless the frequency to be detected is precisely known. The device makes possible the use of a reduced bandwidth, because the analyte to be detected in each chamber is known and may be pre-determined, and the coated nanoparticles and/or the chamber/coil geometry can be specifically customized for detection of the specific analyte. The RF sensing coils may be tuned to the required frequency(ies). Use of a uniform magnetic field eliminates a variable in determining the required frequency(ies). Multiple analytes may still be detected, since different chambers can be customized for detection of different analytes, for example, by use of different binding moieties on the nanoparticles in the different chambers and/or by tuning sensing coils located about, in proximity to, or in relation to the respective chambers.

Although it is preferable to use narrow band excitation, in certain embodiments, it may be desirable to use RF excitation broad-banded enough to cover resonance at multiple magnetic field values within an area of interest, for example, where there is a non-uniform magnetic field, where the magnetic field at chamber(s) of interest is unknown, where there are multiple chambers, and/or where there is a single RF excitation coil (or group of coils), e.g., located outside the body (particularly, where excitation is not tuned to a single chamber or location). In certain embodiments, the magnetic field at a given chamber location may be detected by a sensor located at or near the chamber and this information used by the processor 208 to determine the appropriate Larmor frequency(ies) needed (in which case, one or more narrow band RF excitation(s) is appropriate). FIG. 3B is a schematic diagram of in vivo RF excitation of a biological sample in the presence of a non-uniform magnetic field (gradient magnetic field $B_G$ 352). In certain embodiments, the gradient may be a calibrated gradient provided along with excitation broad-banded enough to cover resonance at all field values within a region of interest 302. For example, where there is a single signal 354 received from an area of interest containing more than one chamber (308, 310), the signal may be processed by application of Fourier transform or equivalent, and portions of the signal associated with their respective chambers as a function of signal frequency 356. In addition to use of a calibrated or measurable magnetic field gradient, other manipulations of the magnetic field may be used to obtain position information and/or detect and separate signals from various chambers of an implanted device. For example, in certain embodiments, the magnetic field changes in time. In certain embodiments, a rotating (or otherwise moving) field gradient is used, for example, where linear positioning information is collected along a number of different directions. In this way, the magnetic field varies in three dimensions, not just two. Varying the magnetic field may facilitate location of one or more chambers of an implanted device, determination of and/or application of appropriate excitation signal(s), detection of echo signal(s), and/or association of one or more echo signals (e.g. portions thereof) with corresponding chambers.

Element 210 of the system of FIG. 2 represents a reader, typically disposed ex vivo. The reader may include, for example, logic circuitry that processes sensed signals into parameters such as T2, T1, T2*, and/or T1ρ, and/or logic circuitry which uses one or more of these parameters to compute values of analyte concentration (where "concentration" includes any indication of relative amount of an analyte). The sensed signals may be the echo signals themselves, portions thereof, or signals that are associated with such signals. For example, where an implanted RF sensing coil is used, there is preferably some processing, such as amplification, rectification, and/or digitization, which is performed in proximity to the coil (e.g. on a chip supporting, containing, or close to the coil—e.g. within 5 mm, 1 mm, 0.5 mm, or 0.1 mm). The detected signal may be transmitted via an antenna from the RF sensing coil to the reader 210, and further processed. In certain embodiments, the reader 210 is an optional component (indicated in FIG. 2 by dotted lines), for example, where the system is used to monitor analyte concentration for control of drug release, all processing being performed within the implanted drug monitoring/control device.

In addition to the elements described above, the reader 210 may also include, for example, a memory for storing calibration data, data characterizing magnetic field strength, and correlations for computation of analyte concentration. The reader 210 may include one or more components of the processor 208, described above, one or more of the magnet(s) 204 described above, one or more of the RF coil(s) 206 described above, one or more telemetry components 212 described below, and/or one or more power source components 216 described below.

Element 212 of the system of FIG. 2 represents telemetry component(s) of the system. This may include location determination components associated with RFID tagging; ultrasound imaging; x-ray imaging; infrared, thermal, photoacoustic, near-IR, visible, fluorescent, or other electromagnetic radiation-based imaging systems. The telemetry component(s) may be used to determine "location"

of a sensor and/or chamber(s) within a sensor, where "location" means x,y,z location; x,y location; and/or location relative to an anatomical structure, relative to another element of the system, and/or relative to a known location. Determining "location" may simply mean associating a received echo signal (or portion thereof) with a particular implanted sensor (or particular chamber within a sensor). It is not always necessary to determine an x,y,z location associated with a volume being analyzed.

In certain embodiments in which the magnetic field strength(s) at the chamber(s) is/are known as a function of position, the telemetry component(s) 212 detect the position(s) of the chamber(s) of the sensor, the processor 208 determines the corresponding Larmor frequency(ies), and an RF pulse at, near, or including the Larmor frequency(ies) are applied via the RF excitation coil(s) 206. In certain embodiments, magnetic field sensors 214 are used to determine the magnetic field strength at a desired location. For example, a magnetic field sensor 214 may include a coil, magnetic inductor, and/or other component(s) in proximity to a given chamber of an implanted sensor that determines magnetic field strength at the given chamber. Where magnetic field strength is known, a precise x,y,z or x,y location may not be needed, as long as the signal(s) detected by the RF sensing coil(s) may be attributed to the appropriate chamber/sensor.

Where the RF sensing coil(s) are miniaturized and positioned about each individual chamber, the telemetry components 212 may include one or more antennas—for example, a small, 1 mm-or-less antenna—that operates at a frequency different from that of the RF excitation to transmit one or more unprocessed or, preferably, at least partially processed echo signals to a receiving antenna located outside the body, for example, within or associated with the reader 210.

Element 216 of the system of FIG. 2 represents one or more power source component(s). The power source may be electrical, for example, via wires, or the power source may be one or more batteries, which may be implanted with the sensor and/or which may remain outside the body, for example, in the reader. For example, a lithium ion battery may be used as the power source and may be either implanted or used outside the body (e.g. in the reader).

In certain embodiments, the power source 216 is (or includes) a high frequency (e.g. from 200 to 700 MHz, preferably from 250 to 500 MHz, or more preferably at about 330 MHz) RF signal. This frequency (or frequency range) may also be used for communication of signals from implanted sensors to an external reader. The use of high frequency RF signal as power source allows powering of an implanted system without use of a heavy implanted battery and without skin-penetrating wires. High frequency radio signals have been used, for example, to power pressure sensors that have been implanted in tissue-like stratified media at depths of 5 and 10 cm (see, for example, Miranda et al, "Validation of a Radio Frequency Telemetry Concept in the Presence of Biological Tissue-Like Stratified Media," *Antennas and Propagation Society International Symposium*, IEEE, June 2004, Vol. 2, pp. 1335-1338). Powering of systems via RF signal (which may also be used for communication) can therefore be performed with systems implanted at depths of up to about 5 mm, up to about 10 mm, up to about 2 cm, up to about 5 cm, up to about 8 cm, up to about 10 cm, and possibly at greater depths.

Figure 4A:
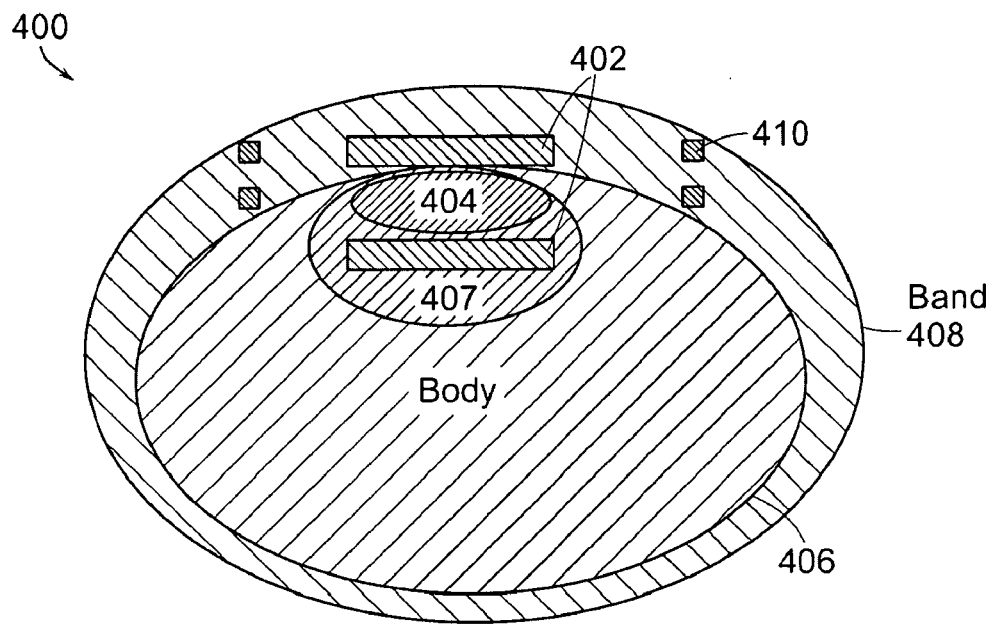
FIG. 4A is a schematic diagram of an NMR system for in vivo detection/monitoring of the presence and/or concentration of analyte(s) in a biological fluid, where one or more magnets and the magnetic-particle-containing chamber(s) are implanted near the surface of the body, according to an illustrative embodiment of the invention.

FIG. 4A is a schematic diagram of an NMR system 400 for in vivo detection/monitoring of the presence and/or concentration of analyte(s) in a biological fluid, where one or more magnets 402 and the magnetic-particle-containing chamber(s) 404 are implanted near the surface of the body 406. Here, "near the surface" can be, for example, at depths of up to about 5 mm, up to about 10 mm, up to about 2 cm, up to about 5 cm, up to about 8 cm, up to about 10 cm, and possibly at greater depths. The implanted unit 407 may be a single, consolidated device, or the unit may be implanted as two or more separate parts. The chamber(s) 404 may include one or more compartments made from a semi-permeable membrane that retains superparamagnetic nanoparticles within the compartments but allows biological fluid to flow, diffuse, or be drawn through the compartments.

A band 408 containing RF excitation and/or sensing coils 410 is placed about the circumference of the body (e.g. a body part such as an arm, wrist, finger, torso, neck, leg, foot, etc.) 406. Manual positioning of the band may be sufficient for accurate operation of the system. Manual positioning aids may include, for example, a mark or tattoo on the surface of the skin, one or more physically visible indentations on the skin, and/or a clasping or latching mechanism that allows the band to engage with the implanted device. In general, the magnetic field must be known at the location(s) of the one or more chambers 404 of the implanted device. Where the magnetic field is uniform, the RF sensing coils 410 may be pre-tuned to the proper frequency(ies) to detect the echo signal(s) from the one or more sensing chamber(s) 404. Where the magnetic field is nonuniform (e.g., where a single-sided magnet is used either externally or implanted), one or more telemetry components 212 described herein above may be used to determine the magnetic field at the location of the one or more chambers 404, thereby enabling calculation of the associated Larmor frequency(ies). The reader 210 may be incorporated in the band, for example, as the face of a watch, or the reader 210 may be attached to the band via a cord.

Figure 4B:
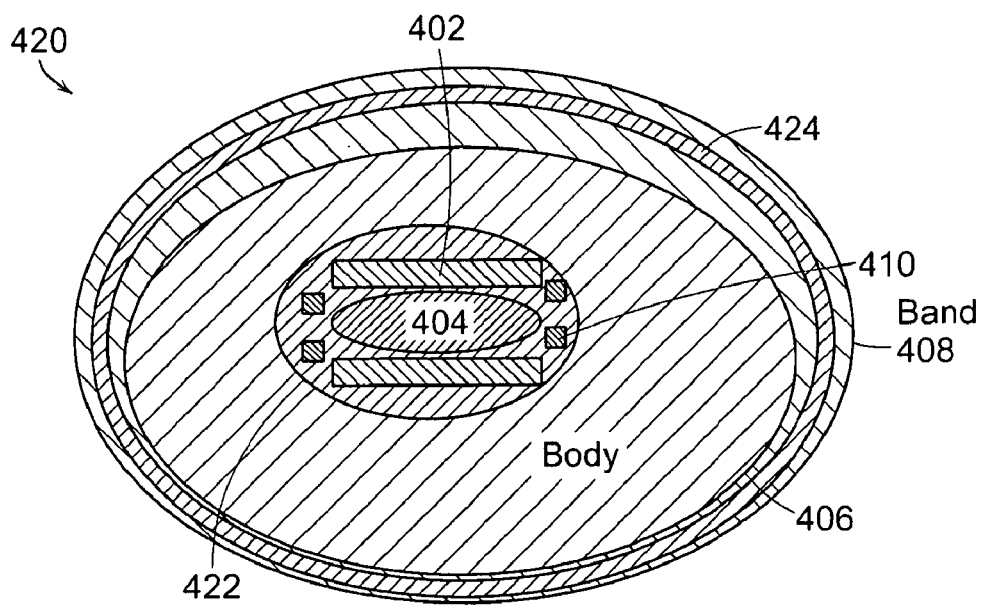
FIG. 4B is a schematic diagram of an NMR system for in vivo detection/monitoring of the presence and/or concentration of analyte(s) in a biological fluid, where one or more magnets, RF sense and/or excitation coil(s), signal processing electronics, an RF communication antenna, and the magnetic-particle-containing chamber(s) are implanted in the body, according to an illustrative embodiment of the invention.

FIG. 4B is a schematic diagram 420 of an NMR system for in vivo detection/monitoring of the presence and/or concentration of analyte(s) in a biological fluid, where one or more magnets 402, RF sense and/or excitation coil(s) 410, signal processing electronics, an RF communication antenna, and the magnetic-particle-containing chamber(s) 404 are implanted in the body. In certain embodiments, the implanted unit 422 may be implanted at a depth of up to about 1 cm, up to about 5 cm, up to about 10 cm, up to about 15 cm, up to about 20 cm, up to about 25 cm, up to about 30 cm, up to about 35 cm, or up to about 40 cm, or more. Because the implanted unit 422 contains RF sensing and/or excitation coil(s) 410, along with transmission antenna, on board, it may generally be implanted deeper in the body than the implanted device 407 of FIG. 4A. The implanted unit 422 may be a single, consolidated device, or the unit may be implanted as two or more separate parts. The chamber(s) 404 may include one or more compartments made from a semi-permeable membrane that retains superparamagnetic nanoparticles within the compartments but allows biological fluid to flow, diffuse, or be drawn through the compartments.

A band 408 containing a receiving antenna 424 is placed about the circumference of the body (e.g. a body part such as an arm, wrist, finger, torso, neck, leg, foot, etc.) 406. Manual positioning of the band may be sufficient for accurate operation of the system. Manual positioning aids may include, for example, a mark or tattoo on the surface of the skin, one or more physically visible indentations on the skin, and/or a clasping or latching mechanism that allows the band to engage with the implanted device. In general, the magnetic field must be known at the location(s) of the one or more chambers 404 of the implanted device. Because the magnet(s) are implanted with the device and the location of the chamber(s) 404 are known with respect to the known magnetic field, the implanted RF sensing coils 410 may be pre-tuned to the proper frequency(ies) to detect the echo signal(s) from the one or more sensing chamber(s) 404. The magnetic field may be either uniform or nonuniform. The reader 210 may be incorporated in the band 408, for example, as the face of a watch, or the reader 210 may be attached to the band via a cord.

Figure 4C:
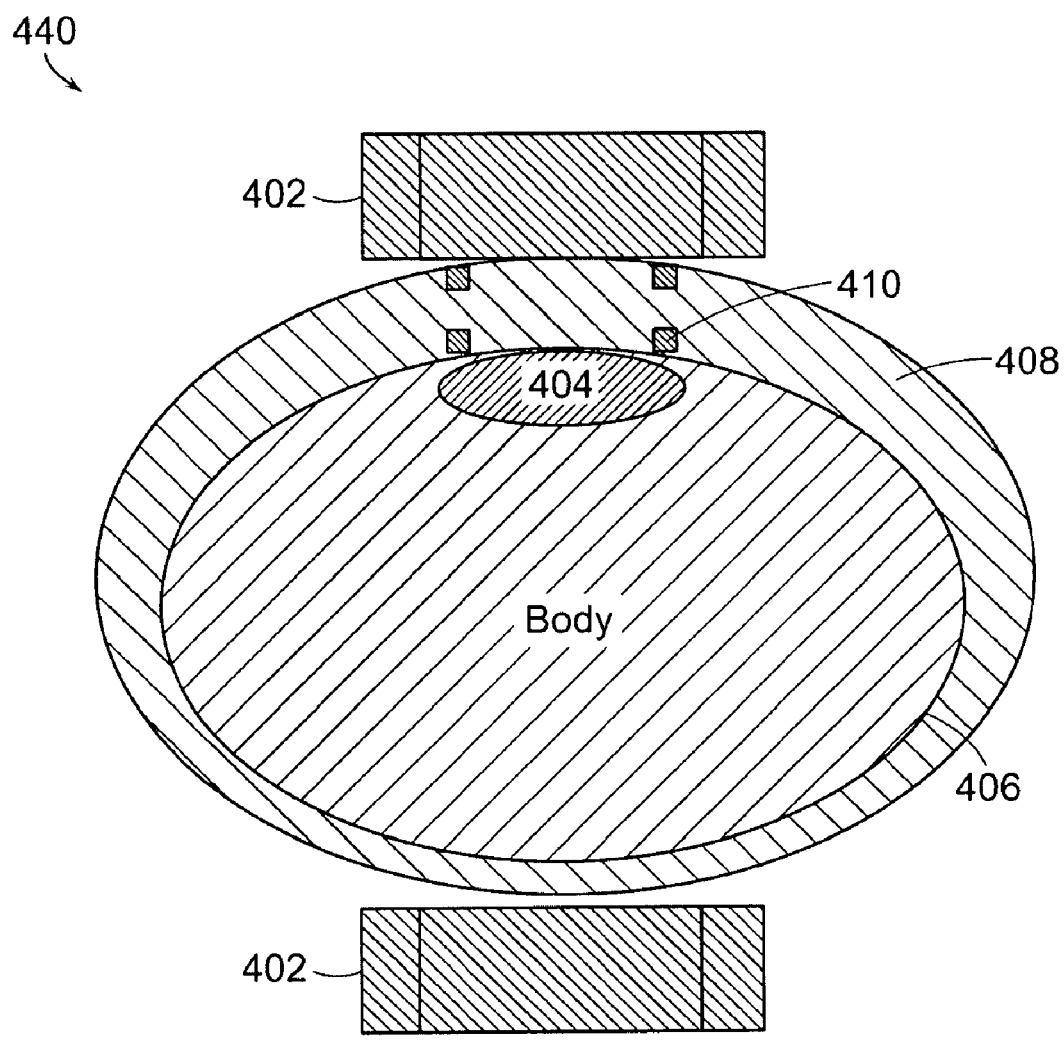
FIG. 4C is a schematic diagram of an NMR system for in vivo detection/monitoring of the presence and/or concentration of analyte(s) in a biological fluid, where magnetic-particle-containing chambers are implanted near the surface of the body, according to an illustrative embodiment of the invention.

FIG. 4C is a schematic diagram 440 of an NMR system for in vivo detection/monitoring of the presence and/or concentration of analyte(s) in a biological fluid, where magnetic-particle-containing chambers 404 are implanted near the surface of the body. Of the systems of FIGS. 4A, 4B, and 4C, the system of FIG. 4C is the least invasive, in that only the particle-containing chambers 404 are implanted near the surface of the body 406. Here, "near the surface" can be, for example, at depths of up to about 2 mm, up to about 3 mm, up to about 5 mm, up to about 10 mm, up to about 2 cm, up to about 5 cm, up to about 8 cm, up to about 10 cm, and possibly at greater depths. The chamber(s) 404 may include one or more compartments made from a semi-permeable membrane that retains superparamagnetic nanoparticles within the compartments but allows biological fluid to flow, diffuse, or be drawn through the compartments.

A band 408 containing RF excitation and/or sensing coils 410 is placed about the circumference of the body (e.g. a body part such as an arm, wrist, finger, torso, neck, leg, foot, etc.) 406. Manual positioning of the band may be sufficient for accurate operation of the system. Manual positioning aids may include, for example, a mark or tattoo on the surface of the skin, one or more physically visible indentations on the skin, and/or a clasping or latching mechanism that allows the band to engage with the implanted device. One or more magnets 402 may be positioned within the band and/or on the outside of the band 408 to provide a magnetic field in the region of the chambers 404. In general, the magnetic field must be known at the location(s) of the one or more chambers 404 of the implanted device. Where the magnetic field is uniform, the RF sensing coils 410 may be pre-tuned to the proper frequency(ies) to detect the echo signal(s) from the one or more sensing chamber(s) 404. Where the magnetic field is nonuniform (e.g., where a single-sided magnet is used), one or more telemetry components 212 described herein above may be used to determine the magnetic field at the location of the one or more chambers 404, thereby enabling calculation of the associated Larmor frequency(ies). The reader 210 may be incorporated in the band, for example, as the face of a watch, or the reader 210 may be attached to the band via a cord.

Figure 5A:
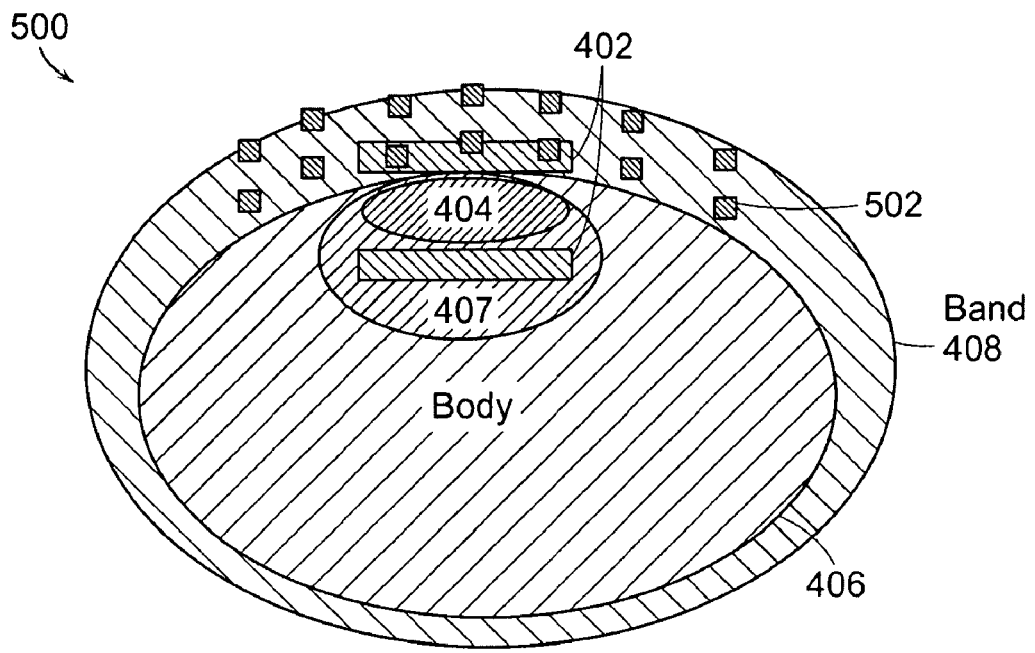
FIG. 5A is a schematic diagram of an NMR system for in vivo detection/monitoring of the presence and/or concentration of analyte(s) in a biological fluid, the system featuring a phased array of sense coils, according to an illustrative embodiment of the invention.

FIG. 5A is a schematic diagram 500 of an NMR system for in vivo detection/monitoring of the presence and/or concentration of analyte(s) in a biological fluid, the system featuring a phased array of sense coils 502. The phased array permits both detection of an echo signal from the nanoparticle-containing chamber(s) 404, as well as location of each of the chamber(s) 404 from which signals are received. A phased array has the added benefit of providing an increased signal to noise ratio of signals received from the surrounded volume. Signals are acquired from mutually isolated receiver coils 502 and associated with the respective chamber from which they originated. Signals may be acquired simultaneously, or there may be switching among multiple coils. From the frequency and amplitude of the monitored signals, both (i) a precise location of one or more sensing chambers may be deduced and (ii) T2 measurement(s) (and/or other measurements derived from the echo signals) from the one or more chambers may be deduced. Further improvements in signal to noise ratio may be achieved using superconducting phased array. In embodiments using superconducting phased array, a super-cooling substance must be well insulated from the patient.

In one embodiment of the phased array system of FIG. 5A, the system first locates the implantable then accurately measures the T2 (and/or other NMR parameters derived from the echo signal(s)) of the implanted or submersed unit. A sequenced combination of the sense coils 502 are used in a "location" mode to determine location of the implanted unit 407. Either singly or in combination, a locator pulse is generated and the echo in all of the nodes are monitored. By observing the time delay, frequency, and amplitude from the different sensors, a precise location may be determined and the proper sense coils can be selected by the electronics logic as the primary echo sense coils from which signal(s) providing T2 and/or other NMR parameters are obtained and analyzed. There may be focusing and/or refocusing pulses applied. A pulse and/or pulse sequence following location may be directed more precisely to the coils 502 best able to receive the proper echo signal(s) corresponding to the desired chamber(s) (404).

In the system 500 of FIG. 5A, one or more magnets 402 and the magnetic-particle-containing chamber(s) 404 are implanted near the surface of the body 406. Here, "near the surface" can be, for example, at depths of up to about 1 mm, up to about 2 mm, up to about 5 mm, up to about 10 mm, up to about 2 cm, up to about 5 cm, up to about 8 cm, up to about 10 cm, and possibly at greater depths. The implanted unit 407 may be a single, consolidated device, or the unit may be implanted as two or more separate parts. The chamber(s) 404 may include one or more compartments made from a semi-permeable membrane that retains superparamagnetic nanoparticles within the compartments but allows biological fluid to flow, diffuse, or be drawn through the compartments.

A band 408 containing a phased array of RF excitation and/or sensing coils 502 is placed about the circumference of the body (e.g. a body part such as an arm, wrist, finger, torso, neck, leg, foot, etc.) 406. Manual positioning of the band may be sufficient for accurate operation of the system. Manual positioning aids may include, for example, a mark or tattoo on the surface of the skin, one or more physically visible indentations on the skin, and/or a clasping or latching mechanism that allows the band to engage with the implanted device. In general, the magnetic field must be known at the location(s) of the one or more chambers 404 of the implanted device. Where the magnetic field is uniform, the RF sensing coils 502 may be pre-tuned to the proper frequency(ies) to detect the echo signal(s) from the one or more sensing chamber(s) 404. Where the magnetic field is nonuniform (e.g., where a single-sided magnet is used either externally or implanted), data obtained from the phased array of coils 502 is used to determine the location of the one or more chambers 404 in relation to the magnet(s), and, therefore, the magnetic field at the location of the one or more chambers 404, thereby enabling calculation of the associated Larmor frequency(ies). The reader 210 may be incorporated in the band, for example, as the face of a watch, or the reader 210 may be attached to the band via a cord. Additional telemetry components 212, as discussed above, may be optionally used.

Figure 5B:
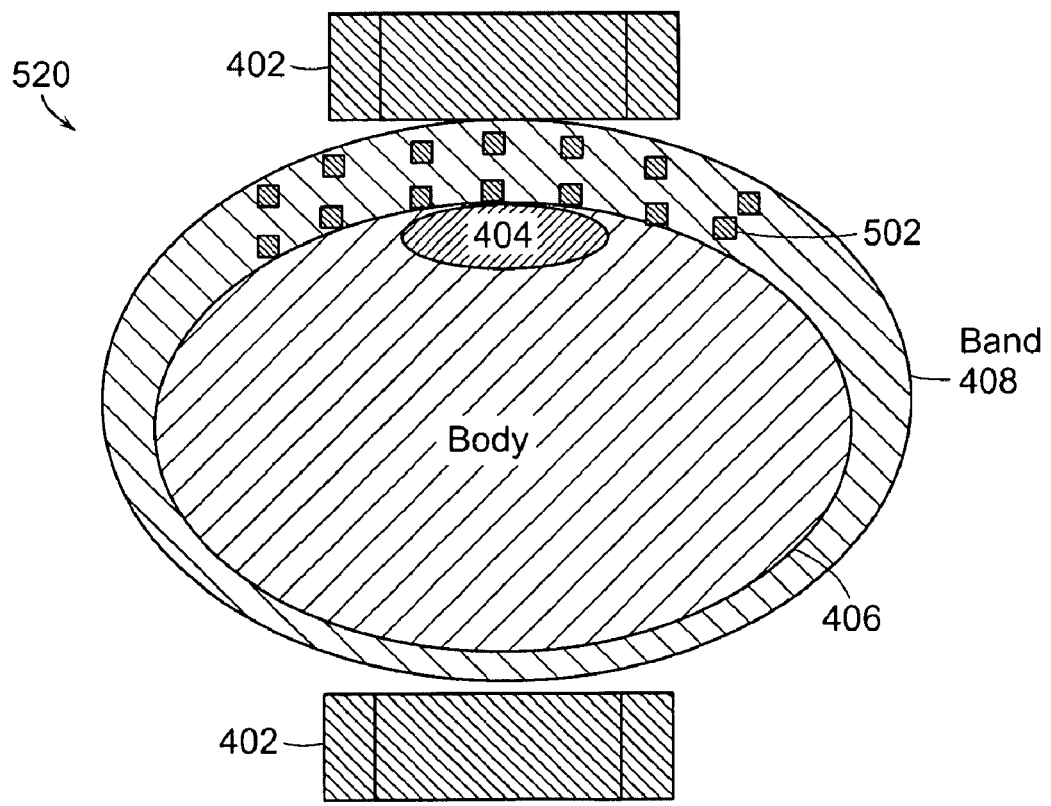
FIG. 5B is a schematic diagram of an NMR system for in vivo detection/monitoring of the presence and/or concentration of analyte(s) in a biological fluid, the system featuring a phased array of sense coils with magnet(s) located outside the body, according to an illustrative embodiment of the invention.

FIG. 5B is a schematic diagram of an NMR system 520 for in vivo detection/monitoring of the presence and/or concentration of analyte(s) in a biological fluid, the system featuring a phased array of sense coils 502 with one or more magnet(s) 402 located outside the body. As in the system of FIG. 5A, magnetic-particle-containing chambers 404 are implanted near the surface of the body; however, the system 520 of FIG. 5B is less invasive in that only the particle-containing chambers 404 are implanted near the surface of the body 406. Here, "near the surface" can be, for example, at depths of up to about 2 mm, up to about 3 mm, up to about 5 mm, up to about 10 mm, up to about 2 cm, up to about 5 cm, up to about 8 cm, up to about 10 cm, and possibly at greater depths. The chamber(s) 404 may include one or more compartments made from a semi-permeable membrane that retains superparamagnetic nanoparticles within the compartments but allows biological fluid to flow, diffuse, or be drawn through the compartments.

A band 408 containing a phased array of RF excitation and/or sensing coils 502 is placed about the circumference of the body (e.g. a body part such as an arm, wrist, finger, torso, neck, leg, foot, etc.) 406. Manual positioning of the band may be sufficient for accurate operation of the system. Manual positioning aids may include, for example, a mark or tattoo on the surface of the skin, one or more physically visible indentations on the skin, and/or a clasping or latching mechanism that allows the band to engage with the implanted device. In general, the magnetic field must be known at the location(s) of the one or more chambers 404 of the implanted device. Where the magnetic field is uniform, the RF sensing coils 502 may be pre-tuned to the proper frequency(ies) to detect the echo signal(s) from the one or more sensing chamber(s) 404. Where the magnetic field is nonuniform (e.g., where a single-sided magnet is used either externally or implanted), data obtained from the phased array of coils 502 is used to determine the location of the one or more chambers 404 in relation to the magnet(s), and, therefore, the magnetic field at the location of the one or more chambers 404, thereby enabling calculation of the associated Larmor frequency(ies). The reader 210 may be incorporated in the band, for example, as the face of a watch, or the reader 210 may be attached to the band via a cord. Additional telemetry components 212, as discussed above, may be optionally used.

FIG. 6A is a schematic diagram of an implanted unit 422 in the NMR system of FIG. 4B 420, according to an illustrative embodiment of the invention. Here, the sensing coil(s) 410, bias magnets (for production of bias magnetic field calibrated in relation to the chamber(s) and/or sensing coil(s)) 402, on-board electronics 602 for at least partially processing echo signals, and a transmitting antenna 604 are all implanted or immersed in the media of interest (e.g. in the body of the subject). The implanted components may be made of and/or coated with polymers, biopolymers, or other biocompatible materials, for example. The substrate pictured 606 is an optional support of the chamber 404 and sensing coil(s) 410. In certain embodiments, the sensing coil(s) 410 also serve as the excitation coil(s). The excitation coil 410 is pictured in FIG. 6A as wrapping around the chamber 404 and sense coil 410 assembly. The echo signal(s) received by the RF sense coil(s) 410 is/are at least partially processed (e.g. are amplified, rectified, and/or digitized) by on-board electronics 602. The proximity of the RF sense coil(s) 410 to the on-board electronics 602 is important in the preservation of the signal, allowing increased sensitivity and providing a Q factor (ratio of the inductive reactance of the RF coil to its resistance at a given frequency, for example, the Larmor frequency) of at least 1, at least about 5, at least about 10, at least about 20, at least about 30, at least about 40, at least about 50, at least about 60, at least about 70, at least about 80, at least about 90, at least about 100, or at least about 125. The at least partially processed signal is transmitted via an antenna 604 to a reader 210 outside (or on the surface of) the body. In certain embodiments, the antenna is about 0.5 mm, about 0.75 mm, about 1 mm, about 1.5 mm, or about 2 mm long, and may be any shape that provides adequate transmission (see telemetry components 212 described above). In one embodiment, a frequency of about 330 MHz is used for power and communications (see telemetry components 212 described above), and one or more frequencies at or about the Larmor frequencies for the one or more chambers are used to generate the echo signals. Where the magnetic field is about 1 T, the Larmor frequency will be about 45 MHz, which is sufficiently different from the frequency used for power and communications to avoid interference.

FIG. 6B is a schematic diagram of the implanted unit 422 of FIG. 6A, where there are a plurality of nanoparticle-containing chambers 404. The telemetry component(s) allow transmission of one or more echo signals that are processed to produce T2 and/or other NMR parameters that can be associated with their respective chamber 404.

Figure 7:
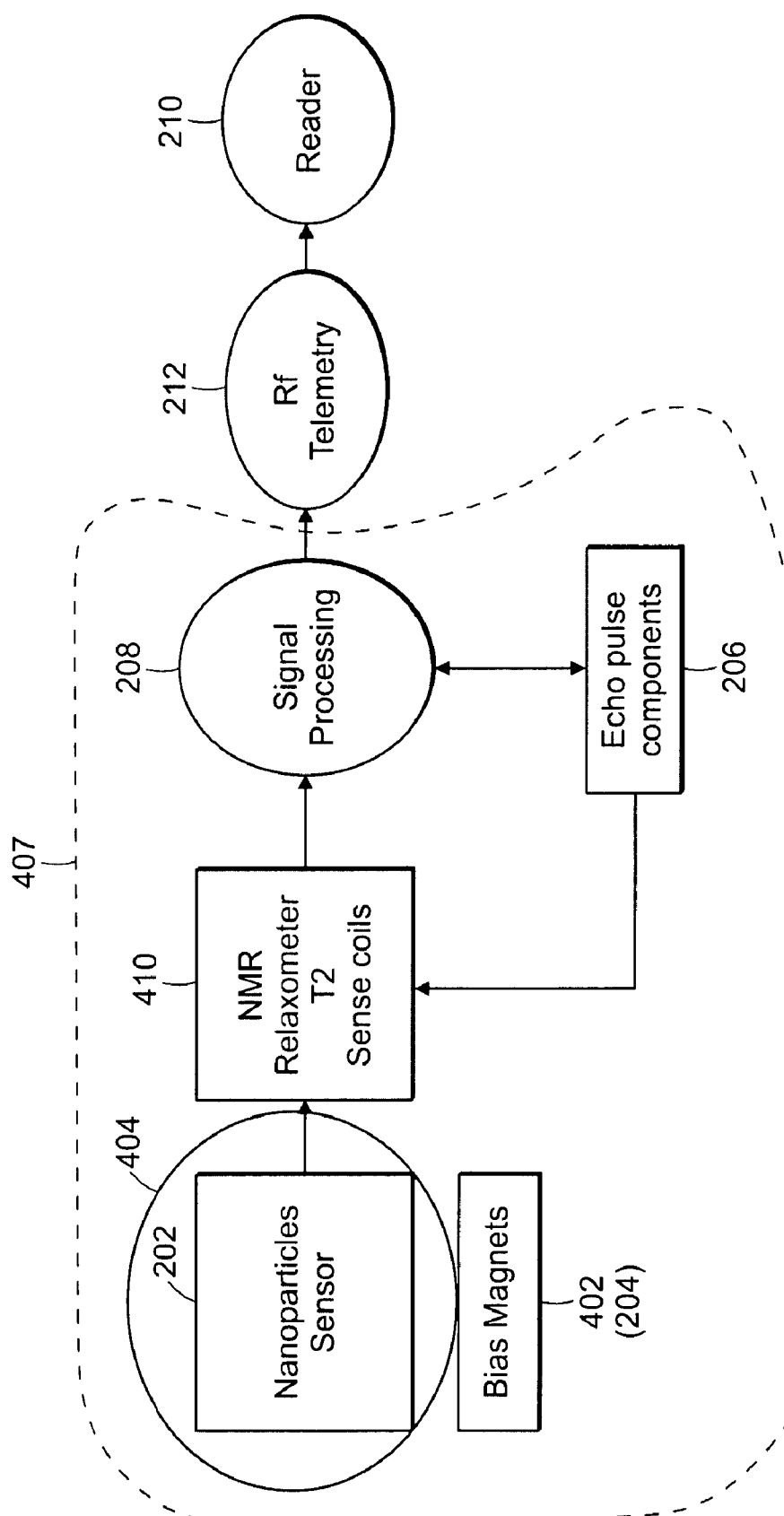
FIG. 7 is a block diagram of components of the NMR system of FIG. 4B with implanted unit and telemetry components, according to an illustrative embodiment of the invention.

FIG. 7 is a block diagram 700 of components of the NMR system of FIG. 4B with implanted unit 404 and with telemetry components 212. Superparamagnetic nanoparticles 202 are held within one or more chambers (e.g. semipermeable membranes or other retention means) 404 and a bias magnetic field is applied (e.g. via permanent bias magnets 402). An RF pulse (or sequence of pulses) 206 is applied at about the Larmor frequency (or at frequencies near to and/or including the Larmor frequency) for each of the chambers, depending on the magnetic field at each respective chamber, and echo signals are received. The signals are at least partially processed 208 and the processed signals (or other data therefrom) are transmitted via RF telemetry (or other telemetry method) 212 to a reader 210 located outside the body.

Figure 8:
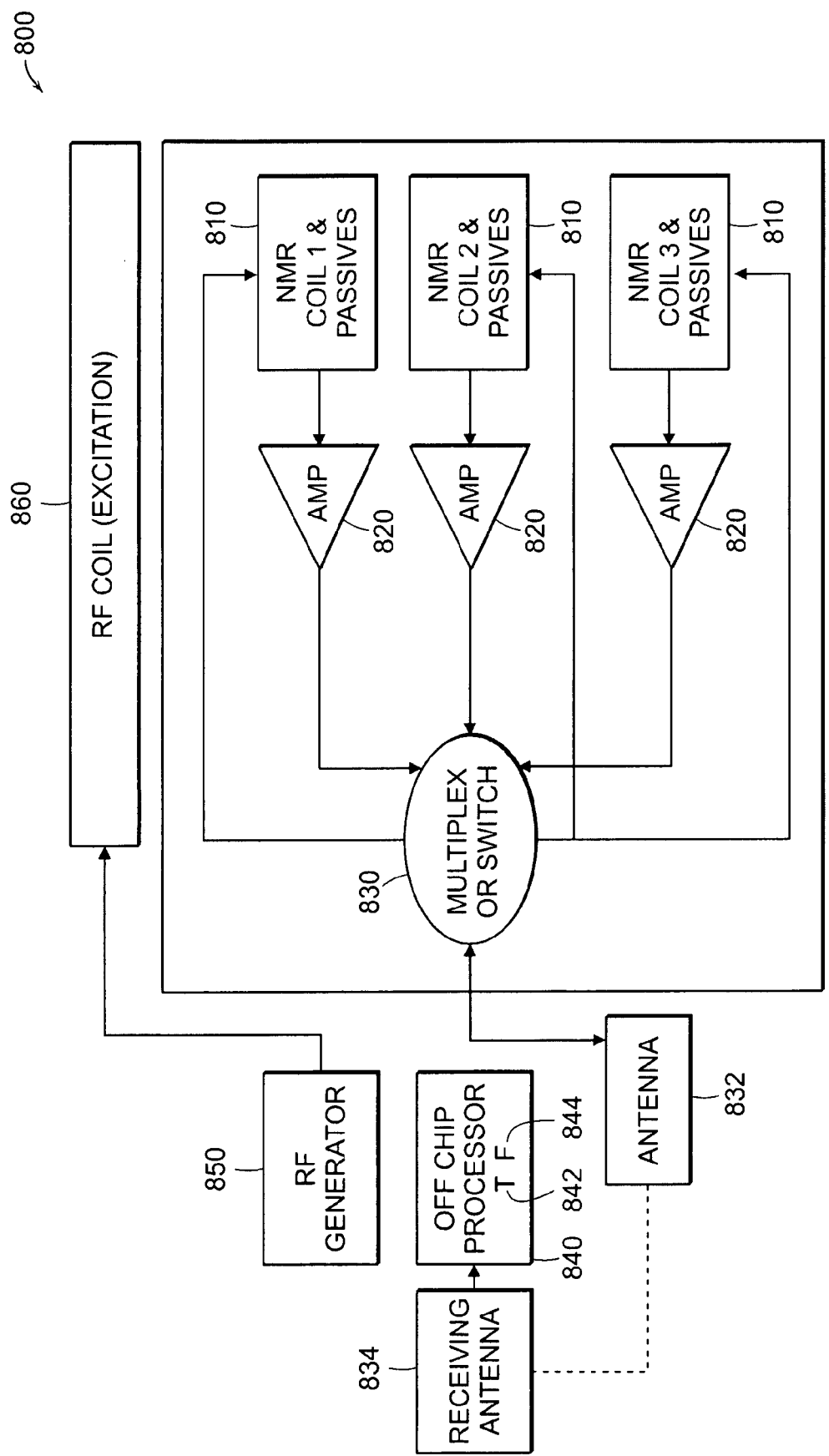
FIG. 8 is a block diagram of components of the NMR system of FIG. 4B with implanted unit, telemetry components, and multiple chambers and sensing coils, according to an illustrative embodiment of the invention.

FIG. 8 is a block diagram 800 of components of the NMR system of FIG. 4B with implanted unit, telemetry components, and multiple chambers and sensing coils. The system as pictured includes an RF coil 860 devoted to providing an excitation pulse/pulse sequence. The RF excitation coil 860 may be implanted or may be ex vivo. In alternative embodiments, the RF excitation is provided by the RF sensing coils. The block diagram 800 includes basic circuit elements in this configuration. The RF sensing coils and associated passives are represented at 810, where the associated passives include inductors, resistors and/or capacitors for the appropriate frequency response from the corresponding chamber. Each signal is amplified by an on-chip amplifier 820 and either is multiplexed 830 to the off-chip processor 840 (via transmitting antenna 832 and receiving antenna 834 operating at a frequency different from the Larmor frequencie(s)—e.g. at least 100 MHz, at least 150 MHz, at least 200 MHz, at least 250 MHz, at least 300 MHz, at least 325 MHz, at least 350 MHz, or at least 400 MHz, for example) or is sequentially switched 860 to the off-chip processor 840 (via transmitting antenna 832 and receiving antenna 834). The switching is practical because, for example, with 100 sample chambers in sequence, the elapsed processing time would be about 50 seconds or less with a single echo pulse lasting about 500 ms. The off chip processor 840 manages the data and performs both time domain 842 and frequency domain 844 analysis to detect the effects of the nanoparticle aggregation. An RF generator 850 drives the excitation RF coil 860 at (or about) the appropriate Larmor frequency given the bias magnet field at the location of the various chambers (where the magnetic field is uniform, the Larmor frequency will be approximately the same for each chamber, but may differ where the composition of the different chambers differs). Where RF excitation is provided by the sensing coils, the coils may be individually tuned to the appropriate frequency(ies) given the composition of the fluid within the chamber (e.g. magnetic particles in contact with biological fluid). The RF generator 850 may or may not be controlled by the off chip processor 840.

The above-described systems of the invention may be used, for example, to measure local analyte concentration in biological fluid in vivo. In this sense, such systems are "in vivo" in that the biological fluid under analysis remains within the body during testing or may be reintroduced into the body following testing.

In one example, in vivo NMR systems described herein may be used by physicians to scan glands for the over- or under-secretion of a protein or other bioactive substance. This may have value, for example, for real time analyte detection during surgery, to provide valuable information that impacts decisions made during the surgical procedure. One example is in the surgical resection of parathyroid adenomas. In this condition, generally one of the four parathyroid glands is overproducing parathyroid hormone (PTH). Traditionally, doctors measure pre-operative PTH levels via laboratory tests, make a best guess, remove the gland, wait, and measure PTH post-removal.

In one embodiment, superparamagnetic particles are conjugated with antibodies to PTH (the antibodies are bound or otherwise attached to the particles). These prepared particles may be injected into the local blood stream or otherwise made to come into contact with the biological fluid, and an NMR device as described herein is used to detect local concentration(s)—relative and/or absolute—of PTH in real time, in vivo, during surgery. The device can then identify the regions with the highest PTH concentration and/or produce a readout of the spatial distribution of concentration, enabling surgical interpretation and allowing more definitive identification of the adenoma prior to its removal. This is of great value where the adenoma is of insufficient size for current physical detection techniques prior to excision—although not physically distinguishable from healthy glands, such adenomas may produce profound endocrine effects systemically. Removal of the incorrect gland(s) can leave the patient in a state of permanent hypoparathyroidism, requiring life-long medication. The NMR device according to embodiments described herein is portable, small, and/or is otherwise convenient for use in a surgical (or clinical) setting to determine/monitor analyte concentrations in real time.

In one embodiment, superparamagnetic nanoparticles conjugated to a target-specific antibody are injected or otherwise introduced into the local blood supply preoperatively and/or intraoperatively. Concentration of the target is determined in real time (or near real-time) using an NMR system as described herein above. This concentration is used during surgery to guide surgical decisions, for example, the identification and removal of parathyroid adenoma.

This method may be applied in any medical setting, for example, those in which relative local concentrations are important. For example, during surgery for breast cancer, if no obvious metastases are detected, patients are injected with a dye or radioactive substance to determine if seeding of axiallary lymph nodes has occurred. Using the NMR systems described herein could enable detection of lymph nodes seeded with cancerous cells in real time, during surgery.

More generally, this method may be used to detect relative concentrations of a substance in vivo. For example, to conform delivery of a drug to a particular target in the body, magnetic particles conjugated to a target-specific antibody can be injected or otherwise introduced into the local blood supply pre and post application of the drug, and a hand-held (or otherwise convenient) NMR system described herein can be used to detect a change (relative or absolute) in local concentration of the drug (or related substance). This can be of value, for example, to insure that the drug reaches its target, where the drug is used in the treatment, diagnosis, and/or detection of cancer, inflammatory bowel disease, gastric reflux, and/or delivery across the blood brain barrier.

Thus, in certain embodiments, the invention includes a method including the steps of injecting a magnetic particle conjugated to a target-specific antibody into the local blood supply pre- or intra-operatively, and detecting concentration of the target with an NMR device/system as described herein. This method provides the ability to detect relative and/or absolute concentrations of an analyte in vivo based on a local different. the difference may be due to variations in local production levels of a substance or differences in concentration over time, for example. An advantage of real time detection of local differences is that surgeons may make pre- and intra-operative decisions based on reliable data to avoid causing harm, for example, by removal of a non-diseased gland. This is particularly important in parathyroid surgeries, but may also be useful in procedures to remove one of multiple potential overproducing glands, in general. Similarly, in the case of a pituitary adenoma, this approach may limit the amount of tissue required to be removed. Other applications of this method includes, for example, identification of lymph node metastases, such as in breast cancer diagnosis and treatment, other tumor/adenoma localization, screening for endocrine disorders, and/or cancer screening in a pre-operative setting.

In certain embodiments, the NMR devices applied in such methods include features described herein (for example, in FIG. 2), in concert with a catheter, needle, stent, shunt, or other lumen for holding, containing, or directing biological fluid for NMR analysis using superparamagnetic nanoparticles.

An embodiment includes particles enclosed within a container/compartment on the outer surface of a needle. A similar design can be used with a catheter, stent, or shunt. For example, a needle or a catheter with a compartment containing magnetic particles described herein (e.g., MRS magnetic resonance switch particles) can be prepared, where the particles are specific to an analyte in question. In the case of parathyroid adenomas, MRS particles may be bound with antibodies to parathyroid hormone (PTH). FIGS. 9A, 9B, 10A, and 10B show catheter and needle devices 900, 920, 1000, 1020, 1040 that may be used with NMR systems described herein. The device may have one or more openings enabling sampling of fluid from the surrounding space, the fluid including blood, intraglandular fluid, and/or other desirable bodily fluid. The device could, as appropriate, also include a coil sufficient to enable NMR-mediated reading according to the in vivo systems described herein. In certain embodiments, most or all components of the NMR system are external to the body and can be used to make assessments of the concentration in real time. In certain embodiments, the biological fluid under analysis remains within the body during testing or may be reintroduced into the body following testing (e.g. as in a catheter or stent); however, certain embodiments are not limited to in vivo applications. The device may be inserted into the patient at an appropriate depth to penetrate the desired target/fluid, and at the appropriate location, at which point in vivo measurement of the fluid using the NMR system is made. In certain embodiments, the device penetrates the body to a depth less than about 1 cm.

The device may be used to detect a normal or abnormal concentration of an analyte. If the tissue is of appropriate size and deemed abnormal such that tissue removal would provide a therapeutic benefit, such as in the case of parathyroid adenomas, the same needle may be used to remove some or all of the gland. In general, the device is inserted into the body to detect analyte concentration using an NMR system as described herein. The assessment may be continuous, for example, so long as the device is in the desired location and/or compartment of the body. Where abnormal analyte concentration is detected, the diseased or otherwise affected tissue may be removed through one or more draws on the syringe device 1000, 1020, 1040.

For example, in a patient with a parathyroid adenoma, the syringe 1000, 1020, 1040, in combination with one or more NMR systems described herein, may be used to detect/monitor the concentration of PTH in one or more suspect parathyroid glands to determine the presence of adenoma. If abnormal levels are detected, the same syringe used in detection may be used to remove the abnormal gland from the body.

These devices can be used to continuously monitor any desirable analyte in flowing fluids (human or other animal), for example, in the catheter embodiments 900, 920. For example, small molecules, drugs, proteins, organisms, and/or other substances may be detected in blood, urine, and/or other in situ biological fluids. This enables continuous, semi-continuous, or intermittent monitoring of analytes whose concentrations change rapidly physiologically, pathologically, and/or with intervention (e.g., PTH, epinephrine, norepinephrine, cortisol, and the like). The devices may also be applied in any system where localized concentrations may be altered, such as with endocrine disorders, neural disorders, etc. Multiple chambers containing paramagnetic particles as described herein can be spatially oriented to detect spatial variance in concentration within a plurality of tissue chambers or locations. Embodiments of the invention may be used, for example, where the target is otherwise difficult and/or painful to access through conventional routes (e.g. cerebrospinal fluid), or where multiple sites exist (e.g. the parathyroid). Surgical removal may be applied, for example, where the targets are small (e.g. parathyroid glands).

The devices 900, 920, 1000, 1020, 1040 may be used to detect/monitor relative and/or absolute concentrations—be they local or systemic concentrations—of an analyte in vivo, continuously, semi-continuously, or intermittently. These devices may further be used (e.g. particularly the needle devices 1000, 1020, 1040) to act on the real time concentration information obtained, e.g., during surgery, or during other medical procedures. Real time analyte assessment provides the patent and/or surgeon better information for decision making during surgery (e.g. removal of the correct parathyroid), for detecting changes in real time before systemic responses (e.g. cortisol), and for enabling less invasive procedures (e.g. needle-based removal of parathyroid adenomas).

Figure 9A:
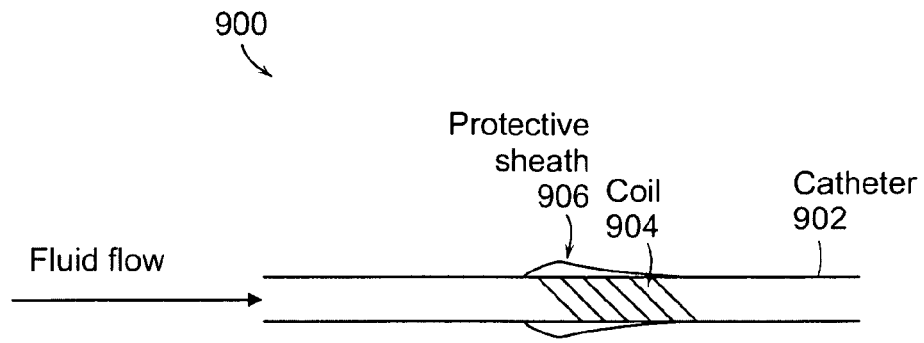
FIGS. 9A and 9B are schematic diagrams of catheter devices that may be used with NMR systems described herein for the in vivo detection of a relative or absolute concentration of analyte as function(s) of position and/or time for real-time analysis of a biological fluid, for example, during surgery to identify and remove parathyroid adenoma, according to an illustrative embodiment of the invention.

The device 900 of FIG. 9A is a catheter 902 equipped with one or more RF coil(s) 904 that surrounds the flow of biological fluid through the catheter. The coil 902 is preferably an echo sensing coil when the device 900 is exposed to a magnetic field, but may also act as an excitation coil. The coil 902 may be positioned within the catheter, may be incorporated within the wall of the catheter, and/or may be located on the outside of the catheter. The catheter 902 is preferably made of a material that will not interfere with particle agglomeration-associated change in T2 or NMR measurement thereof; for example, the catheter may be made of plastic (non-magnetic). The coil 904 may be enclosed, but need not be. Should the portion of the catheter containing the coil 904 be inserted into a patient, it is preferable that the coil be enclosed with a protective sheath 906 and/or coated with a biocompatible material. Detection/monitoring of analyte concentration may be made by NMR systems described herein with the catheter remaining inserted into a patient. The coil 904 may alternately remain outside the body. When the device 900 is used as part of the NMR detection systems described herein, the RF coil 904 can be connected to electronics for signal production and/or processing, and/or the coil 904 may include such electronics.

Binder-coated superparamagnetic nanoparticles 202 can be introduced to the biological fluid being monitored/analyzed by direct injection into a body compartment (e.g. gland or organ) or blood vessel, for example. The particles may be injected proximal to or distal to the site being examined. Subsequently, a desired site (e.g. organ, blood vessel, or other fluid conduit such as a urethra) can be probed. Particles can also be included in the catheter and interfaced with fluid as it passes. Alternatively, as shown in the device 920 of FIG. 9B, particles can be held within the catheter (e.g. within a semipermeable membrane, degradable, or other chamber 922 as described herein), with sample fluid continuously interfacing with the particles during analysis.

Fluid streams of any source may be sampled. Blood vessels may be continuously sampled at a controlled rate sufficient to obtain a reading while not removing an excessive amount of blood from the patient. Body compartments with intermittent fluid flows (e.g. the urethra) may also be sampled with responses dependent on the presence of fluid flow. Samples may also be withdrawn from any compartment containing fluid (e.g. ascities, inflammatory fluid, etc.) by creating a flow of the fluid through the catheter.

Figure 10A:
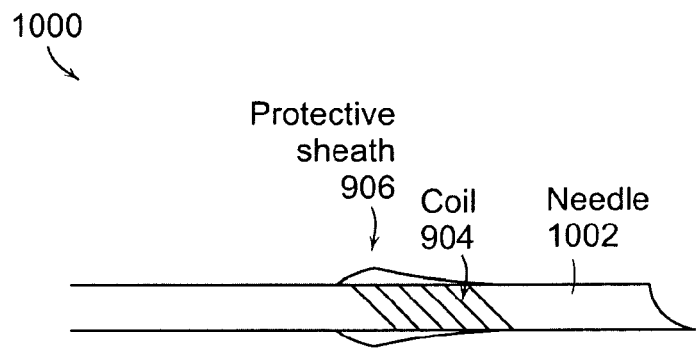
FIGS. 10A and 10B show schematic diagrams of needle devices that may be used with NMR systems described herein for the in vivo detection of a relative or absolute concentration of analyte as function(s) of position and/or time for real-time analysis of a biological fluid, for example, during surgery to identify and remove parathyroid adenoma, according to an illustrative embodiment of the invention.
Figure 10B:
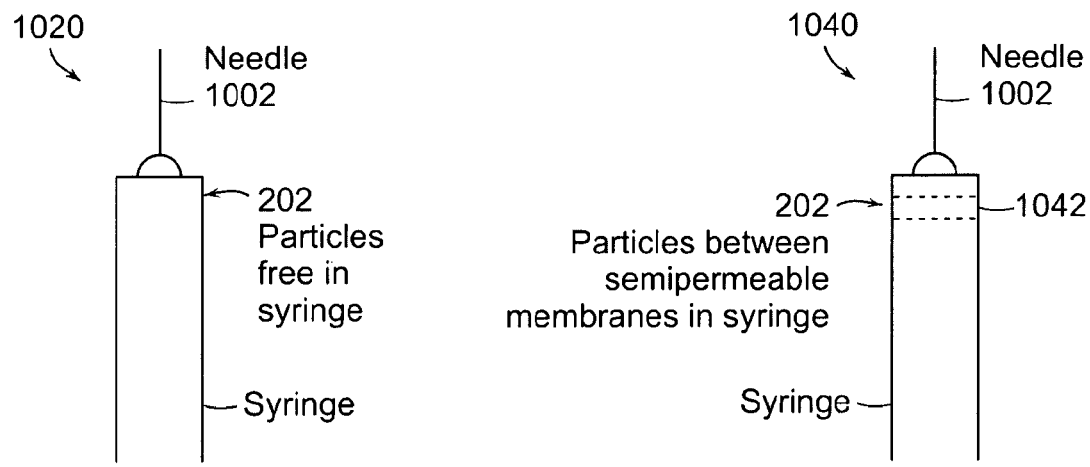

FIG. 10A shows a needle device 1000 equipped with one or more RF coil(s) 904 that surrounds the flow of biological fluid through the needle 1002. The coil 902 is preferably an echo sensing coil when the device 900 is exposed to a magnetic field, but may also act as an excitation coil. The coil 902 may be positioned within the needle, may be incorporated within the wall of the needle, and/or may be located on the outside of the needle. The needle 902 is preferably made of a material that will not interfere with particle agglomeration-associated change in T2 or NMR measurement thereof; for example, the needle may be made of plastic (non-magnetic). The coil 904 may be enclosed, but need not be. Should the portion of the needle containing the coil 904 be inserted into a patient, it is preferable that the coil be enclosed with a protective sheath 906 and/or coated with a biocompatible material. Detection/monitoring of analyte concentration may be made by NMR systems described herein with the catheter remaining inserted into a patient. The coil 904 may alternately remain outside the body. When the device 1000 is used as part of the NMR detection systems described herein, the RF coil 904 can be connected to electronics for signal production and/or processing, and/or the coil 904 may include such electronics.

Binder-coated superparamagnetic nanoparticles 202 can be introduced to the biological fluid being monitored/analyzed by direct injection into a body compartment (e.g. gland or organ) or blood vessel, for example. The particles may be injected proximal to or distal to the site being examined. Subsequently, a desired site (e.g. organ, blood vessel, or other fluid conduit such as a urethra) can be probed. Particles can be included in the needle and interfaced with fluid as it enters the needle, as shown in device 1020 of FIG. 10B. Alternatively, as shown in device 1040 of FIG. 10B, particles can be held within the needle (e.g. within a semi-permeable membrane, degradable, or other chamber 1042 as described herein), with sample fluid drawn into the chamber and interfacing with the particles during analysis.

Figure 9B:
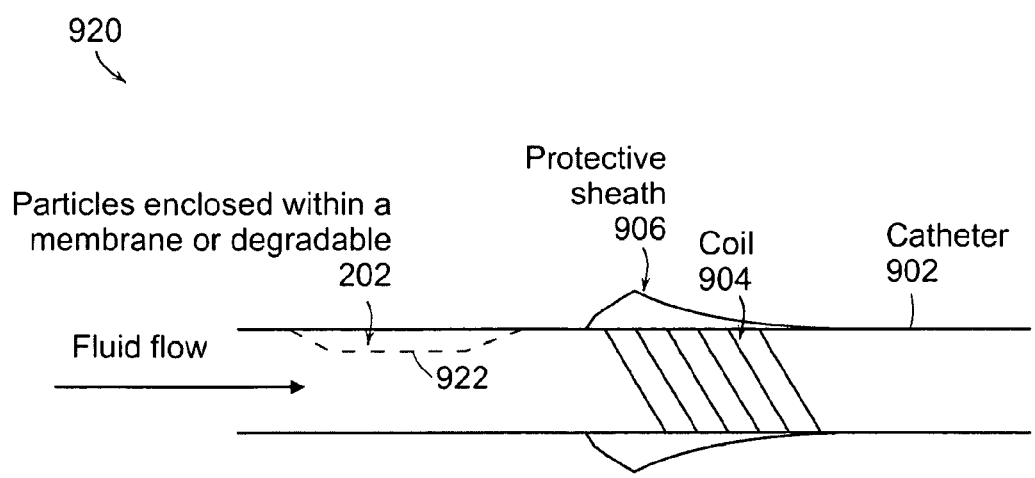

The devices of FIGS. 9A, 9B, 10A, and/or 10B may be used, for example, along with the analyte concentrators of FIGS. 11, 12, and/or 13 of co-pending, co-owned U.S. patent application Ser. No. 11/513,503, filed Aug. 31, 2006, which is incorporated herein by reference.

While this invention has been particularly shown and described with references to example embodiments thereof, it will be understood by those skilled in the art that various changes in form and details may be made therein without departing from the scope of the invention encompassed by the appended claims.

What is claimed is:

1. A method for assessing the presence or concentration of an analyte contained in a body fluid of a mammal in-vivo using a nuclear magnetic resonance system, the method comprising the steps of:
   (a) implanting partially or completely a sensor of the nuclear magnetic resonance system within the mammal's body, the sensor comprising structure defining a sample volume and a port, the sample volume containing magnetic particles, and the port allowing the analyte to enter the sample volume and preventing, partly or completely, the magnetic particles from leaving the sample volume, the extent of aggregation of the magnetic particles being indicative of the presence or concentration of the analyte in the sample volume;
   (b) calculating a Larmor frequency within the sample volume or a portion thereof;
   (c) applying a probe radiofrequency pulse sequence at or near the Larmor frequency to part or all of the sample volume from a reader positioned outside the mammal's body in the presence of a magnetic field to induce echo radiofrequency signals; and
   (d) assessing the presence or concentration of the analyte from the echo radiofrequency signals.

2. The method of claim 1, wherein the magnetic particles are paramagnetic.

3. The method of claim 1, wherein the magnetic particles are superparamagnetic.

4. The method of claim 1, wherein the magnetic particles are functionalized with one or more binding moieties that bind to one or more target analytes.

5. The method of claim 4, wherein at least one of the one or more binding moieties comprises at least one of an amino group, a carboxyl group, a sulfhydryl group, an amine group, an imine group, an epoxy group, a hydroxyl group, a thiol group, an acrylate group, or an isocyano group.

6. The method of claim 4, wherein at least one of the one or more binding moieties comprises at least one of an amino acid, a nucleic acid, an oligonucleotide, a therapeutic agent, a metabolite of a therapeutic agent, a peptide, a polypeptide, a protein, a carbohydrate, a polysaccharide, a virus, or a bacteria.

7. The method of claim 1, wherein at least one of the magnetic particles comprises a polymer matrix coating.

8. The method of claim 1, wherein the magnetic particles have an average particle size of between about 1 nm and 5 μm.

9. The method of claim 1, wherein the sensor comprises a magnetic field detector for detecting the strengths of a magnetic field within or adjacent to the sample volume, and a transmitter for transmitting a signal indicative of the strength of the magnetic field; and wherein the reader comprises a receiver for receiving the signal indicative of the strength of the magnetic field.

10. The method of claim 1, wherein the sensor comprises a transmitting antenna for transmission of data received from a logic circuitry to the reader.

11. The method of claim 10, wherein the logic circuitry is used to calculate the Larmor frequency of water within the sample volume or a portion thereof.

12. The method of claim 1, wherein the sensor comprises a radiofrequency identification (RFID) emitter for emitting radiofrequency signals.

13. The method of claim 1, wherein the sensor comprises a radiofrequency coil for applying the radiofrequency pulse sequence to the sample volume in the presence of the magnetic field.

14. The method of claim 13, wherein the radiofrequency coil acts as a sensing radio frequency coil and an excitation radiofrequency coil.

15. The method of claim 1, wherein the reader comprises a radiofrequency coil for applying the radiofrequency pulse sequence to the sample volume in the presence of the magnetic field and a logic circuitry for calculating the Larmor frequency of water within the sample volume or a portion thereof.

16. The method of claim 15, wherein the radiofrequency coil acts as a sensing radio frequency coil and an excitation radiofrequency coil.

17. The method of claim 15, further comprising a logic circuitry for determining a nuclear magnetic resonance parameter influenced by the analyte within the sample volume.

18. The method of claim 17, wherein the nuclear magnetic resonance parameter is $T_2$.

* * * * *